US009187501B2

(12) United States Patent
Schoenfisch et al.

(10) Patent No.: US 9,187,501 B2
(45) Date of Patent: Nov. 17, 2015

(54) NITRIC OXIDE-RELEASING NANORODS AND THEIR METHODS OF USE

(71) Applicant: The University of North Carolina at Chapel Hill, Chapel Hill, NC (US)

(72) Inventors: Mark H. Schoenfisch, Chapel Hill, NC (US); Yuan Lu, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/011,488

(22) Filed: Aug. 27, 2013

(65) Prior Publication Data

US 2014/0065200 A1 Mar. 6, 2014

Related U.S. Application Data

(60) Provisional application No. 61/694,007, filed on Aug. 28, 2012.

(51) Int. Cl.
| | |
|---|---|
| A61K 9/14 | (2006.01) |
| C07F 7/08 | (2006.01) |
| A61K 49/18 | (2006.01) |
| A61K 47/48 | (2006.01) |
| A01N 59/00 | (2006.01) |
| B82Y 5/00 | (2011.01) |

(52) U.S. Cl.
CPC .............. *C07F 7/0834* (2013.01); *A01N 59/00* (2013.01); *A61K 47/48869* (2013.01); *A61K 49/1884* (2013.01); *B82Y 5/00* (2013.01); *Y10T 428/2975* (2015.01)

(58) Field of Classification Search
CPC .................................................. A61K 49/1884
See application file for complete search history.

(56) References Cited

U.S. PATENT DOCUMENTS

| | | |
|---|---|---|
| 6,610,660 B1 | 8/2003 | Saavedra et al. |
| 6,673,338 B1 | 1/2004 | Arnold et al. |
| 6,841,166 B1 | 1/2005 | Zhang et al. |
| 2006/0095120 A1 | 5/2006 | Herrmann |
| 2009/0214618 A1* | 8/2009 | Schoenfisch et al. ......... 424/426 |

FOREIGN PATENT DOCUMENTS

WO WO 2004/009253 A1 1/2004

OTHER PUBLICATIONS

Bergey, D. H., et al., "*Bergey's Manual of Determinative Bacteriology*", (9th ed., Lippincott Williams & Wilkins.: Baltimore, Maryland) Hensyl and Forlifer, eds. (1994), pp. 532-575.
Carpenter, A. W., et al., "Influence of Scaffold Size on Bactericidal Activity of Nitric Oxide-Releasing Silica Nanoparticles," *American Chemical Society*, 2011, pp. 7235-7244, vol. 5(9).
Fang, F. C. et al., "Mechanisms of nitric oxide-related antimicrobial activity". *J. Clin. Invest.*, 1997, pp. 2818-2825, vol. 99.
Ghaffari, A., et al., "Potential application of gaseous nitric oxide as a topical antimicrobial agent." *Nitric Oxide-Biol. Chem.*2006, pp. 21-29, vol. 14.
Hetrick, E. M., et al., "Bactericidal efficacy of nitric oxide-releasing silica nanoparticles.", *ACS Nano*, 2008, pp. 235-246, vol. 2.
Howell-Jones, R. S., et al., "A review of the microbiology, antibiotic usage and resistance in chronic skin wounds.", *J. Antimicrob. Chemother.*, 2005, pp. 143-149, vol. 55.
Hrabie, J. et al., "Chemistry of the Nitric Oxide-Releasing Diazeniumdiolate ("Nitrosohydroxylamine") Functional Gropu and Its Oxygen-Substituted Derivatives," *Chem. Rev.*, 2002, pp. 1135-1154, vol. 102.
Li, C., et al., "A versatile method to prepare RAFT agent anchored substrates and the preparation of PMMA grafted nanoparticles." *Macromolecules*, 2006, pp. 3175-3183, vol. 39.
Lu, Y., et al., "Structurally Diverse Nitric Oxide-Releasing Poly(propylene imine) Dendrimers.", *Chem. Mater.*, 2011, pp. 4227-4233, vol. 23.
Lu, Y., et al., "Shape- and Nitric Oxide Flux-Dependent Bactericidal Activity of Nitric Oxide-Releasing Silica Nanorods," *Nano Micro Small*, 2013, pp. 1-10, Wiley-VCH Verlag GmbH & Co. KGaA, Weinheim.
Lyczak, J.B., et al., "Establishment of *Pseudomonas aeruginosa*infection: lessons from a versatile opportunist," *Microbes and Infection*, 2000, pp. 1051-1060, vol. 2.
Macmicking, J.; et al., "Nitric oxide and macrophage function". *Annu.Rev. Immunol.*, 1997, pp. 323-350, vol. 15.
McMullin, B. B.; et al., "The antimicrobial effect of nitric oxide on the bacteria that cause nosocomial pneumonia in mechanically ventilated patients in the intensive care unit." *Respir. Care*, 2005, pp. 1451-1456, vol. 50.
Privett, B. J., et al., "Synergy of Nitric Oxide and Silver Sulfadiazine against Gram-Negative, Gram-Positive, and Antibiotic-Resistant Pathogens.", *Mol. Pharm.*, 2010, pp. 2289-2296, vol. 7.
Pruitt, B. A., et al., "Burn wound infections: Current status." *World J. Surg.*, 1998, pp. 135-145, vol. 22.
Riccio, D.A. and Schoenfisch, M.H., "Nitric oxide release: Part I. Macromolecular scaffolds," *Chem. Soc. Rev.*, 2012, pp. 3731-3741, vol. 41.
Shin, J. H., et al., "Synthesis of nitric oxide-releasing silica nanoparticles.", *J. Am. Chem. Soc.*, 2007, pp. 4612-4619, vol. 129.
Smith, A.W., et al., "Biofilms and antibiotic therapy: Is there a role for combating bacterial resistance by the use of novel drug delivery systems?", *Advanced Drug Delivery Reviews*, 2005, pp. 1539-1550, vol. 57.

(Continued)

*Primary Examiner* — Paul Dickinson
(74) *Attorney, Agent, or Firm* — Alston & Bird LLP

(57) ABSTRACT

In one aspect, the subject matter disclosed herein is directed to NO-releasing functionalized nanorods having a desirable aspect ratio. The nanorods are also capable of releasing a desirable amount of NO (nitric oxide). In another aspect, the subject matter disclosed herein is directed to a composition comprising the NO-releasing nanorods. In another aspect, the subject matter disclosed herein is directed to methods of preparing NO-releasing nanorods having a specified aspect ratio. In another aspect, the subject matter disclosed herein is directed to a method of combating infection comprising administering to a subject a composition comprising NO-releasing nanorods, wherein the nanorods have a specified aspect ratio and NO-release profile.

20 Claims, 12 Drawing Sheets

(56) References Cited

OTHER PUBLICATIONS

Stein, A., et al., "Hybrid Inorganic-Organic Mesoporous Silicates-Nanoscopic Reactors Coming of Age," *Advanced Materials*, Oct. 2, 2000, pp. 1403-1419, vol. 12(19), Wiley-VCH, Weinheim, Germany.

Yang, H., et al., "The role of defects in the formation of mesoporous silica fibers, films, and curved shapes.", *Adv. Mater.*, 1998, pp. 883-887, vol. 10.

Wolf, L.K., "Nitric Oxide-Emitting Nanomaterials Kill Microbes", *Chemical & Engineering News*, Sep. 5, 2011, pp. 54-55, vol. 89(36).

Freireich, E. J., et al., "Quantitative Comparison of Toxicity of Anticancer Agents in Mouse, Rat, Hamster, Dog, Monkey, and Man," *Cancer Chemotherapy Reports*, May 1966, pp. 219-244, vol. 50.

Hayakawa, K. and Kwak, J. C. T., "Interactions Between Polymers and Cationic Surfactants," Cationic Surfactants, In: Surfactant Science Series; Gorddard, E. D., Ananthapadmanabham, K. P., Eds.; Marcel Dekker: New York, 1991, pp. 189-248.

Marletta, M. A., et al., "Unraveling the biological significance of nitric oxide," *BioFactors*, 1990, pp. 219-225, vol. 2.

\* cited by examiner

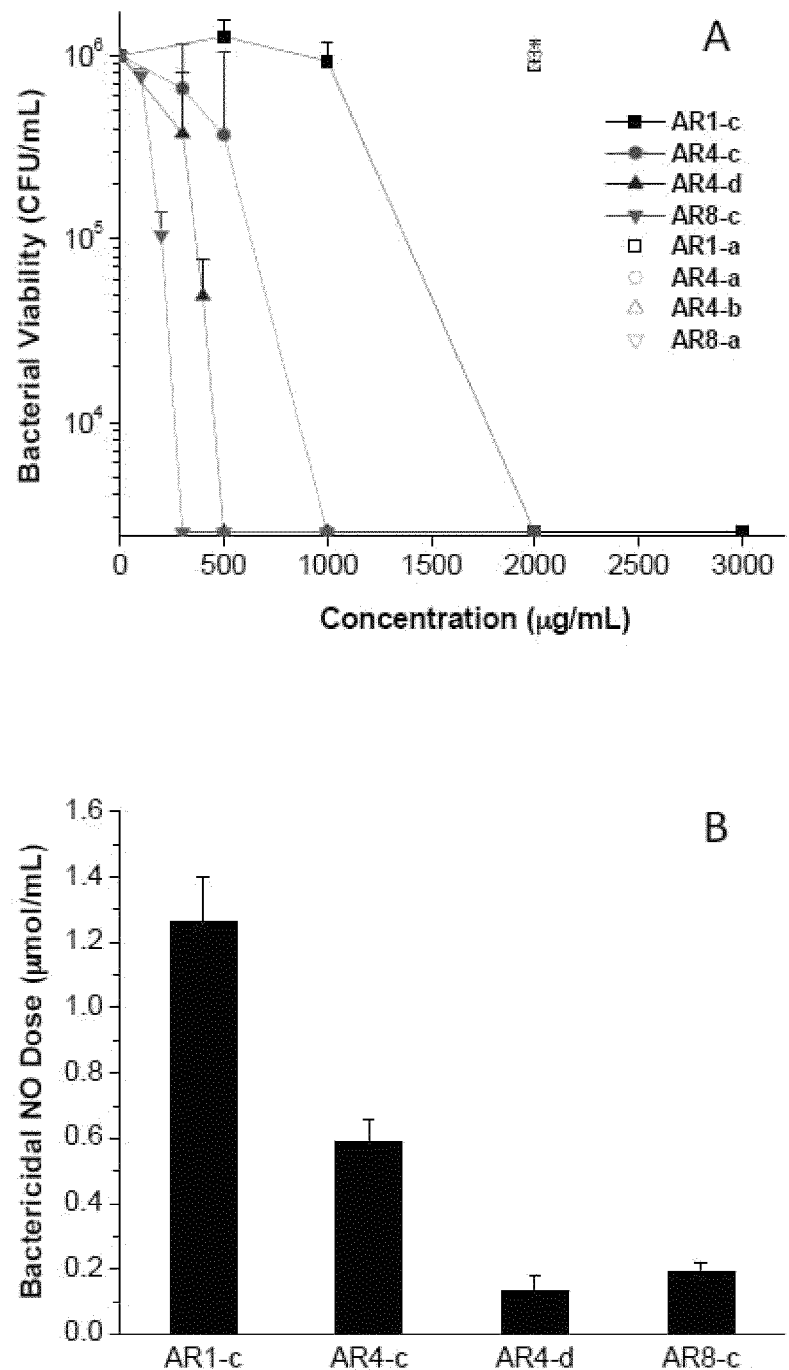
Figure 5A & B

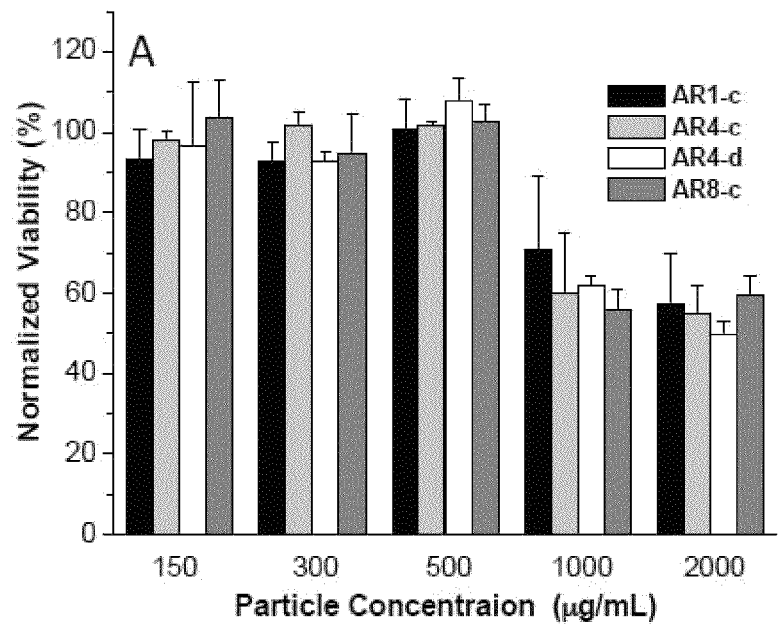
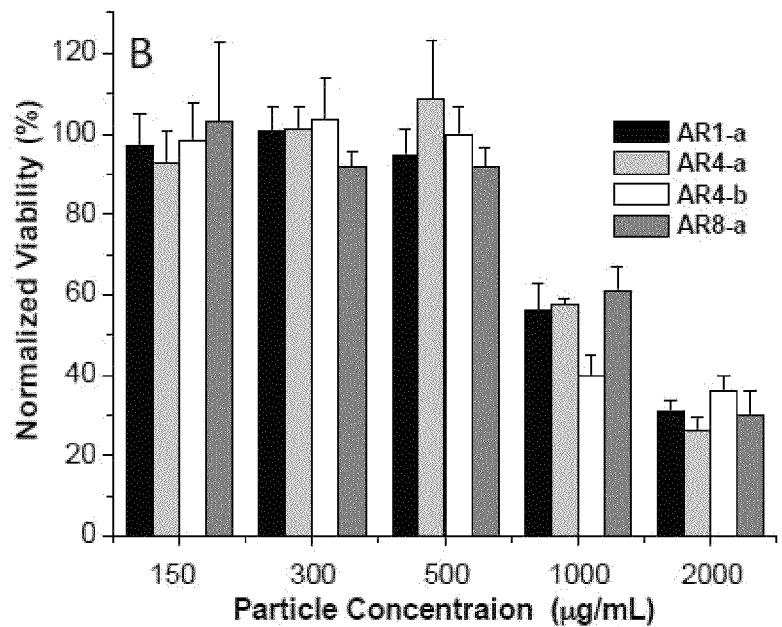
Figure 6A & B

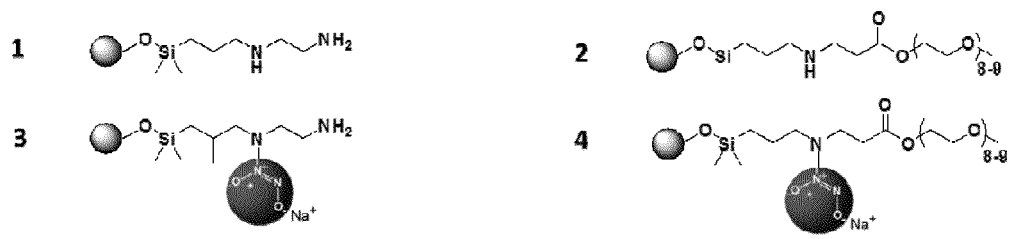
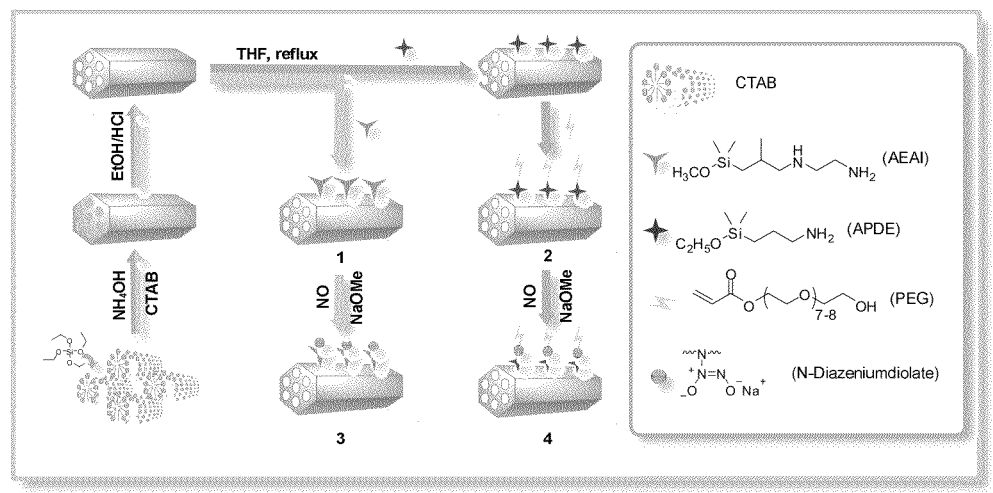
Figure 8

FIGURE 10A, B & C

NITRIC OXIDE-RELEASING NANORODS AND THEIR METHODS OF USE

CROSS-REFERENCE TO RELATED APPLICATIONS

This application claims the benefit, under 35 U.S.C. §119, of U.S. Provisional Patent Application Ser. No. 61/694,007, filed Aug. 28, 2012, the disclosure of which is incorporated herein by reference in its entirety.

GOVERNMENT SUPPORT

This invention was made with government support under Grant EB000708 awarded by the National Institutes of Health. The government has certain rights in the invention.

FIELD OF THE INVENTION

The subject matter herein is directed to NO releasing nanorods.

BACKGROUND

Nitric oxide (NO), a diatomic free radical produced endogenously by macrophages and other inflammatory cells, plays a key role in the natural immune response to pathogens. (Marletta, M. A., Tayeh, M. A., Hevel, J. M., Unraveling the biological significance of nitric oxide. *Biofactors* 1990, 2, 219-25; MacMicking, J.; Xie, Q. W.; Nathan, C., Nitric oxide and macrophage function. *Annu. Rev. Immunol.* 1997, 15, 323-350). Both NO and its reactive byproducts (e.g., peroxynitrite and dinitrogen trioxide) exert significant oxidative and nitrosative stress on bacterial cells to facilitate their killing. (Fang, F. C., Mechanisms of nitric oxide-related antimicrobial activity. *J. Clin. Invest.* 1997, 99, 2818-2825). Nitrosative stress acts to nitrosate thiols influencing protein and DNA function, while lipid peroxidation via oxidative stress destroys the bacterial membrane integrity. (Fang, 1997). Methods for delivering exogenous NO are thus actively being developed against both Gram-positive and Gram-negative bacteria. (Ghaffari, A., Miller, C. C., McMullin, B., Ghahary, A., Potential application of gaseous nitric oxide as a topical antimicrobial agent. *Nitric Oxide-Biol. Chem.* 2006, 14, 21-29; Hetrick, E. M., Shin, J. H., Stasko, N. A., Johnson, C. B., Wespe, D. A., Holmuhamedov, E., Schoenfisch, M. H., Bactericidal efficacy of nitric oxide-releasing silica nanoparticles. *ACS Nano* 2008, 2, 235-246; Privett, B. J., Deupree, S. M., Backlund, C. J., Rao, K. S., Johnson, C. B., Coneski, P. N., Schoenfisch, M. H., Synergy of Nitric Oxide and Silver Sulfadiazine against Gram-Negative, Gram-Positive, and Antibiotic-Resistant Pathogens. *Mol. Pharm.* 2010, 7, 2289-2296). While gaseous NO from a cylinder and NO delivered from small molecule NO donors have proven to be antimicrobial, (Hetrick, 2008; McMullin, B. B.; Chittock, D. R.; Roscoe, D. L.; Garcha, H.; Wang, L.; Miller, C. C., The antimicrobial effect of nitric oxide on the bacteria that cause nosocomial pneumonia in mechanically ventilated patients in the intensive care unit. *Respir. Care* 2005, 50, 1451-6) macromolecular scaffolds are more potent due to their ability to deliver large localized concentrations of NO. (Hetrick, 2008; Privett, 2010) The ability to achieve larger NO payloads and improved bactericidal efficacy using NO-releasing dendrimers and silica particles, relative to small molecule NO donors has been reported. (Hetrick, 2008; Shin, J. H., Metzger, S. K., Schoenfisch, M. H., Synthesis of nitric oxide-releasing silica nanoparticles. *J. Am. Chem. Soc.* 2007, 129, 4612-4619; Lu, Y., Sun, B., Li, C. H., Schoenfisch, M. H., Structurally Diverse Nitric Oxide-Releasing Poly(propylene imine) Dendrimers. *Chem. Mater.* 2011, 23, 4227-4233)

Bacterial infections are of concern. Bacteria typically exist in biofilms. Bacteria cause a large number of diseases and chronic illness with generalized symptoms, such as headache, nausea, vomiting, abdominal cramps, sore throat, sore eyes, and fever that may make an accurate diagnosis difficult.

The presently disclosed subject matter addresses, in whole or in part, these and other needs in the art.

SUMMARY OF THE INVENTION

In one aspect, the subject matter disclosed herein is directed to nanorods that have specified aspect ratios, are capable of releasing NO at desired levels and, in some embodiments, have bactericidal activity.

In another aspect, the subject matter disclosed herein is directed to a composition comprising NO-releasing nanorods, wherein the nanorods have specified aspect ratios, are capable of releasing NO at desired levels and, in some embodiments, have bactericidal activity.

In another aspect, the subject matter disclosed herein is directed to a method of preparing NO-releasing nanorods having specified aspect ratios, are capable of releasing NO at desired levels and, in some embodiments, have bactericidal activity.

In another aspect, the subject matter disclosed herein is directed to a method of combating infection comprising administering to a subject a composition comprising NO-releasing nanorods, wherein the nanorods have specified aspect ratios and are capable of releasing NO at desired levels.

BRIEF DESCRIPTION OF THE FIGURES

FIGS. 5A & B depict minimum bactericidal concentrations (A) and bactericidal NO doses (B) of NO-releasing (solid symbols) SNRs against *S. aureus* in PBS. Control nanorods (open symbols) resulted in no significant viability reduction at 2000 µg/mL.

FIGS. 6A & B depict toxicity of NO-releasing (A) and control (B) SNRs to L929 mouse fibroblasts.

FIG. 8 depicts a synthetic route for preparing certain silica nanorods disclosed herein.

DETAILED DESCRIPTION

Figure 1:
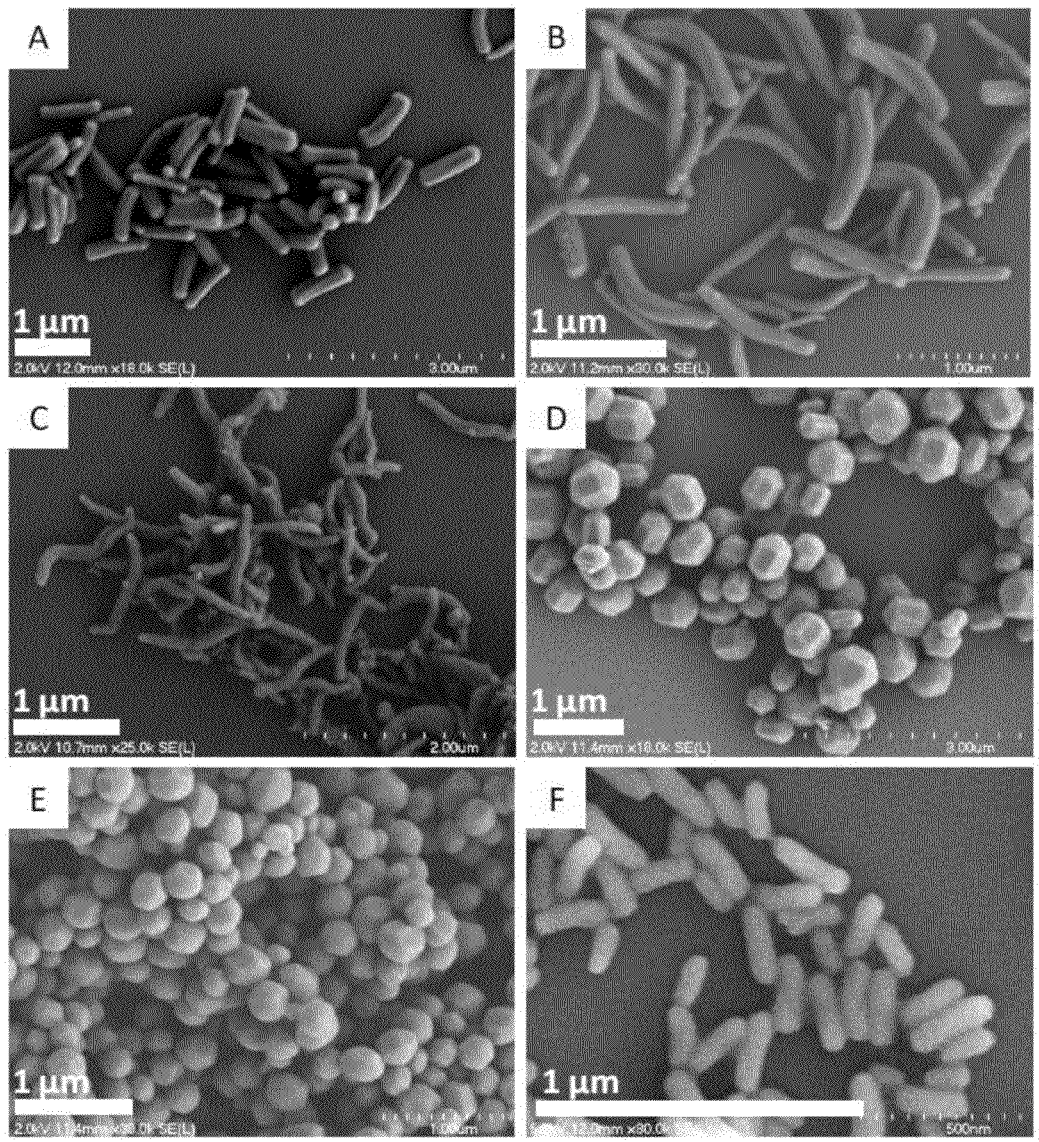
FIGS. 1A, B, C, D, E & F depict scanning electron microscopy (SEM) images of silica nanorods with different morphologies. Aspect ratios of these particles that are in the general shape of nanorods were 4.5±0.9 (A); 8.0±1.0 (B); 9.4±0.7 (C); 1.2±0.5 (D); 1.1±0.1 (E); and 3.1±0.3 (F), respectively.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims.

Mesoporous silica nanorods (SNRs) were synthesized and then functionalized with an aminoalkoxysilane, also referred to herein as a mono, di or trialkoxysilane, to prepare a new class of nitric oxide (NO)-releasing materials. The aspect ratio and size of the SNRs were tuned by varying the temperature, pH, and silane concentration used during the surfactant-templated synthesis. Advantageously, a preferred aspect ratio has been produced that provides excellent bactericidal efficacy as determined, for example, through in vitro testing.

N-Diazeniumdiolates nitric oxide (NO) donors were formed on the secondary amine-functionalized SNRs by reaction with NO gas under basic conditions. Nanorod surface modifications were employed to manipulate the NO-release kinetics. The diverse morphology (i.e., aspect ratio ~1-8), NO-release kinetics (2000-14000 ppb NO/mg nanorod) and similar size (i.e., nanorod volume ~0.02 μm$_3$) of the resulting NO-releasing SNRs facilitated further study of how nanorod shape and NO flux impacts bactericidal activity against Gram-positive *Staphylococcus aureus* (*S. aureus*), which has a relatively thick peptidoglycan layer, and Gram-negative *Pseudomonas aeruginosa* (*P. aeruginosa*) bacteria, which has a relatively thin peptidoglycan layer. The bactericidal efficacy of these materials improved with increasing nanorod aspect ratio and NO flux ($NO_{max}$). As disclosed herein, both chemical (i.e., NO-release kinetics) and physical (i.e., morphology) properties greatly influenced the bactericidal activity of these materials.

The term "mesoporous" as used herein in reference to particles in the general shape of a nanorod means a nanorod that contains a plurality of pores. The pores can range from about 2 nm to about 50 nm in diameter. In embodiments, the surfactant micelles can act as porogens.

The term "nanorod" as used herein means an object that has a length that is greater than its width. However, as shown in FIGS. 1A-F and FIGS. 3A-L, the rod-shaped particles disclosed herein can have a length or width in the microns, e.g. more than 1,000 nm in length with corresponding widths that provide the desired aspect ratio. Thus, micro-sized rods having stored NO and capable of releasing NO are also described. Preferably, the aspect ratio is at least 1, which may include a rod-like or cube shape. More preferably, the aspect ratio is at least 4. Thus, the particles are of a general rod-shape having nano or micro-sized proportions.

As used herein, the term "aspect ratio" means the proportional relationship between a nanorod's length and its width. The aspect ratio is described as the length divided by the width.

As used herein, the term "monodisperse" refers to a plurality of nanorods where essentially each nanorod is substantially similar to every other nanorod in the plurality. As used herein, a monodisperse plurality of nanorods preferably means that substantially all of the nanorods will have the desired aspect ratio of at least about 1. More preferably, essentially all of the nanorods will have essentially the same aspect ratio of at least about 4. Also preferred is a monodisperse plurality wherein each nanorod has essentially the same aspect ratio that is from about 6 to about 10. Most preferably, essentially all of the nanorods will have an aspect ratio of about 8. In these embodiments, it is also preferred that the nanorods are capable of releasing NO at the desired levels described elsewhere herein.

As used herein, the term "plurality" refers to two or more. In embodiments, the plurality refers to all of the nanorods in a sample or composition.

As used herein the term "subject" refers to humans as well as all other animals. It is understood that guinea pigs, dogs, cats, rats, mice, horses, goats, cattle, sheep, zoo animals, livestock, primates, and humans are all examples of animals within the scope of the meaning of the term.

As used herein, a subject "in need thereof" may be a subject whom could have been but is not required to have been diagnosed as suffering from the condition intended to be treated. In one aspect, the present method is directed to conditions that are noticeable to the subject and the subject wishes to treat or ameliorate the condition without a formal diagnosis. Alternatively, a subject could be diagnosed with a bacterial infection and seek treatment or amelioration by a method disclosed herein. Accordingly, a mammal in need thereof may be one who has been diagnosed as having a condition and is in need of specific treatment or is susceptible to the condition. In all cases, the subject or someone treating the subject will have appreciated the need for treatment.

As used herein the term "treating" is intended to refer to all processes wherein there may be a slowing, interrupting, arresting, or stopping of the progression of the condition or symptoms and does not necessarily indicate a total elimination of the underlying condition. The terms also encompass administration wherein the subject has a condition or symptom or a predisposition towards a condition or symptom, where the purpose is to cure, heal, alleviate, relieve, alter, improve or affect the condition or symptom or the predisposition to the same.

Also contemplated is preventing the condition or symptom or the predisposition to the same by prophylactic administration.

As used herein, the term "bactericidal" refers to a nanorod's property for killing or treating bacteria and/or a biofilm. The nanorods described herein may also be bacteriostatic, which refers to the property for arresting bacteria growth and/or formation of a biofilm.

As used herein, the term "therapeutically effective" and "effective amount," is defined as the amount of the composition that produces at least some effect in treating a disease or a condition. Though the effective amount of active compound(s) used for therapeutic treatment varies depending upon the manner of administration, the age, body weight, and general health of the subject, it is routine for one of skill in this field, such as an attending physician or veterinarian to determine the appropriate amount and dosage regimen using the guidance provided herein alone or in combination with state of the art. Such amounts may be referred to as "effective" amounts.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-5}$ straight-chain alkyls. In other embodiments, "alkyl" refers, in particular, to $C_{1-5}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —$NR^1R''$, wherein $R^1$ and $R''$ can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, f-butoxyl, and pentoxyl. The term "oxyalkyl" can be used interchangeably with "alkoxyl". In some embodiments, the alkoxyl has 1, 2, 3, 4, or 5 carbons.

"Aralkyl" refers to an aryl-alkyl group wherein aryl and alkyl are as previously described, and included substituted aryl and substituted alkyl. Exemplary aralkyl groups include benzyl, phenylethyl, and naphthylmethyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

"Arylene" refers to a bivalent aryl group. An exemplary arylene is phenylene, which can have ring carbon atoms available for bonding in ortho, meta, or para positions with regard to each other, i.e., respectively. The arylene group can also be napthylene. The arylene group can be optionally substituted (a "substituted arylene") with one or more "aryl group substituents" as defined herein, which can be the same or different.

"Aralkylene" refers to a bivalent group that contains both alkyl and aryl groups. For example, aralkylene groups can have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-).

The term "amino" and "amine" refer to nitrogen-containing groups such as $NR_3$, $NH_3$, $NHR_2$, and $NH_2R$, wherein R can be alkyl, branched alkyl, cycloalkyl, aryl, alkylene, arylene, aralkylene. Thus, "amino" as used herein can refer to a primary amine, a secondary amine, or a tertiary amine. In some embodiments, one R of an amino group can be a cation stabilized diazeniumdiolate (i.e., $NONO^-X^+$). The terms "cationic amine" and "quaternary amine" refer to an amino group having an additional (i.e., a fourth) R group, for example a hydrogen or an alkyl group bonded to the nitrogen. Thus, cationic and quaternary amines carry a positive charge.

The term "alkylamine" refers to the -alkyl-$NH_2$ group.

The term "carbonyl" refers to the —(C=O)— group.

The term "carboxyl" refers to the —COOH group and the term "carboxylate" refers to an anion formed from a carboxyl group, i.e., —$COO^-$.

The terms "halo", "halide", or "halogen" as used herein refer to fluoro, chloro, bromo, and iodo groups.

The term "hydroxyl" and "hydroxyl" refer to the —OH group.

The term "hydroxyalkyl" refers to an alkyl group substituted with an —OH group.

The term "mercapto" or "thio" refers to the —SH group. The term "silyl" refers to groups comprising silicon atoms (Si).

The term "silane" refers to any compound that includes four organic groups, such as including any of the organic groups described herein (e.g., alkyl, aryl and alkoxy), bonded to a silicon atom.

As used herein the term "alkoxysilane" refers to a silane that includes one, two, three, or four alkoxy groups bonded to a silicon atom. For example, tetraalkoxysilane refers to $Si(OR)_4$, wherein R is alkyl. Each alkyl group can be the same or different. An "alkylalkoxylsilane" refers to an alkoxysilane wherein one or more of the alkoxy groups has been replaced with an alkyl group. Thus, an alkylalkoxysilane comprises at least one alkyl-Si bond.

The term "cationic or anionic silane" refers to an alkylsilane wherein one of the alkyl groups is further substituted with an alkyl substituent that has a positive (i.e., cationic) or a negative (i.e. anionic) charge, or can become charged (i.e., is ionizable) in a particular environment (i.e., in vivo).

The term "silanol" refers to a Si—OH group.

In an embodiment, the subject matter described herein is directed to a nitric oxide-releasing nanorod comprising,
 i. a silane, and
 ii. a functionalized mono, di or trialkoxysilane,
wherein the functionalized mono, di or trialkoxysilane comprises a NO-donor molecule; wherein the nitric oxide-releasing nanorod has an aspect ratio of at least 1 and a $[NO]_{max}$ of at least 10 ppb/mg. As disclosed in the methods of preparing the nanorods, a NO-donor molecule is present and, in embodiments, can be covalently bound to the functionalized mono, di or trialkoxysilane.

The nanorods described herein can be mesoporous. In this aspect, the mesoporous nanorods comprise two or more pores having sizes from about 2 nm to about 50 nm. The pores do not have to be uniform in size, although it is contemplated that the pores can be substantially uniform in size and arrangement in embodiments.

The silanes, which also include alkoxysilanes, employed may also be referred to as a silicate and can be one or more tetraalkylorthosilicates having alkyl groups of from 1 to 20 carbon atoms, having the general formula $Si(OR)_4$. Illustrative examples include tetramethylorthosilicate, tetraethylorthosilicate ($Si(OC_2H_5)_4$) (TEOS), and the like. Other useful silanes have the formula $Si(OR)_4$, wherein at least one R is a $C_{1-5}$ alkyl, and the other R groups can be H or substituted alkyl. Preferably, the silane is TEOS or TMOS. Other useful silanes are selected from the group consisting of methyltrimethoxysilane (MTMOS), ethyltrimethoxysilane (ETMOS), butyltrimethoxysilane (BTMOS), propyltrimethoxysilane (PTMOS), butyltriethoxysilane (BTEOS), and octadecyltrimethoxysilane (ODTMOS).

The R groups in the alkoxysilane may be the same or may be different. In particular embodiments, the tetraalkoxysilane may include tetramethoxysilane (TMOS), tetraethoxysilane (TEOS), tetra-n-propoxysilane (TPOS) and/or tetra-n-butoxysilane (TBOS). In some embodiments of the invention, the alkoxysilane may include an alkylalkoxysilane having the formula of R'—$Si(OR)_3$, wherein R' is an organic functional group (e.g., alkyl, aryl or alkylaryl) and each R is independently H, alkyl or substituted alkyl. As such, each R may be the same or may be different and each R group may be the same or different as R'. In particular embodiments, the alkoxysilane may include methyltrimethoxysilane (MTMOS), ethyltrimethoxysilane (ETMOS), propyltrimethoxysilane (PTMOS), butyltrimethoxysilane (BTMOS), butyltriethoxysilane (BTEOS), and/or octadecyltrimethoxysilane (ODTMOS). In some embodiments, the alkoxysilane may include an alkoxysilane having the formula R'R"—Si(OR)$_2$, wherein R' and R" are each independently an organic functional group (e.g., alkyl, aryl or alkylaryl) and each R is independently H, alkyl or substituted alkyl. In some embodiments of the invention, the backbone alkoxysilane may include an alkoxysilane having the formula of R'R"R"'—SiOR, wherein R', R" and R"' are each independently an organic functional group (e.g., alkyl, aryl or alkylaryl) and R is H, alkyl or substituted alkyl.

Examples of alkoxysilanes that may be used in some embodiments include acryloxypropylmethyldimethoxysilane, 3-acryloxypropyltrimethoxysilane, allyltriethoxysilane, allyltrimethoxysilane, amyltriethoxysilane, amyltrimethoxysilane, 5-(bicycloheptenyl)methyltriethoxysilane, 5-(bicycloheptenyl)methyltrimethoxysilane, 5-(bicycloheptenyl)dimethylmethoxysilane, 5-(bicycloheptenyl) methyldiethoxysilane, bis(3-cyanopropyl)diethoxysilane, bis(3-cyanopropyl)dimethoxysilane, 1,6-bis(trimethoxysilyl)hexane, bis(trimethylsiloxy)methylsilane, bromomethyldimethylmethoxysilane, 3-bromopropyltriethoxysilane, n-butyldimethylmethoxysilane, tert-diphenylmethoxysilane, n-butyldimethoxysilane, n-butyldiethoxysilane, n-butyltrimethoxysilane, 2-(carbomethoxy)ethyltrimethoxysilane, 4-chlorobutyldimethylmethoxysilane, 4-chlorobutyldimethylethoxysilane, 2-chloroethyltriethoxysilane, chloromethyldimethylethoxysilane, p-(chloromethyl)phenyltriethoxysilane, p-(chloromethyl)phenyltrimethoxysilane, chloromethyltriethoxysilane, chlorophenyltrimethoxysilane, 3-chloropropylmethyldimethoxysilane, 3-chloropropyltriethoxysilane, 2-cyanoethylmethyltrimethoxysilane, (cyanomethylphenethyl)triethoxysilane, 2-(3-cyclohexenyl)ethylltrimethoxysilane, cyclohexydiethoxymethylsilane, cyclopentyltrimethoxysilane, di-n-butyldimethoxysilane, dicyclopentyldimethoxysilane, diethyldiethoxysilane, diethyldimethoxysilane, diethyldibutoxysilane, diethylphosphatoethyltriethoxysilane, diethyl(triethoxysilylpropyl)malonate, di-n-hexyldimethoxysilane, diisopropyldimethoxysilane, dimethyldimethoxysilane, 2,3-dimethylpropyldimethylethoxysilane, dimethylethoxysilane, diphenydiethoxysilane, diphenyldimethoxysilane, diphenylmethylethoxysilane, 2-(diphenylphosphino)ethyltriethoxysilane, divinylethoxysilane, n-dodecyltriethoxysilane, 2-(3,4-epoxycyclohexyl)ethyltrimethoxysilane, ethyltriethoxysilane, ethyltrimethoxysilane, 3-glycidoxypropyldimethylethoxysilane, (3-glycidoxypropyl)methyldimethoxysilane, 3-glycidoxypropyltrimethoxysilane, n-heptylmethyldimethoxysilane, n-hexadecyltriethoxysilane, 5-hexenyltrimethoxysilane, n-hexytriethoxysilane, n-hexyltnethoxysilane, 3-iodopropyltriethoxysilane, 3-iodopropyltrimethoxysilane, isobutyltrimethoxysilane, isobutyltriethoxysilane, isocyanatopropyldimethylmethoxysilane, 3-isocyanatopropyltriethoxysilane, isooctyltriethoxysilane, 3-mercaptopropyl-methyldimethoxysilane, 3-mercaptopropyltrimethoxysilane, 3-mercaptopropyltriethoxysilane, 3-methacryloxypropylmethyldiethoxysilane, 3-methacryloxypropylmethyldiethoxysilane, 3-methacryloxypropyltrimethoxysilane, 3-(4-methoxyphenyl)propyltrimethoxysilane, methylcyclohexyldiethoxysilane, methyldiethoxysilane, methyldimethoxysilane, methyldodecyldiethoxysilane, methyl-n-octadecyldimethoxysilane, methyl(2-phenethyl)dimethoxysilane, methylphenyldiethoxysilane, methylphenyldimethoxysilane, methyl-n-propyldimethoxysilane, methyltriethoxysilane, neophylmethyldiethoxysilane, n-octadecyldimethylmethoxysilane, n-octadecyltriethoxysilane, n-octadecyltrimethoxysilane, 7-octenyltrimethoxysilane, n-octylmethyldimethoxysilane, n-octyltriethoxysilane, phenethyldimethylmethoxysilane, phenethyltriethoxysilane, phenyldimethylethoxysilane, phenyltriethoxysilane, phenyltriethoxysilane, phthalocyanatodimethoxysilane, n-propyltrimethoxysilane, styrylethyltrimethoxysilane, tetra-n-butoxysilane, tetraethoxysilane, tetrapropoxysilane, (tridecafluoro-1,1,2,2,-tetrahydrooctyl)-1-trimethoxysilane, triethoxysilane, triethoxysilylpropylethyl carbamate, triethylethoxysilane, (3,3,3-trifluoropropyl) methyldimethoxysilane, (3,3,3-trifluoropropyl) triethoxysilane, trimethoxysilane, 1-trimethoxysilyl-2-(p,m-chloromethyl)phenylethane, trimethylethoxysilane, 2-(trimethylsiloxy)ethyl methacrylate, p-trimethylsiloxynitrobenzene, triphenylethoxysilane, n-undeceyltriethoxysilane, vinyldimethylethoxysilane and vinyltrimethoxysilane.

Useful aminoalkoxysilanes, referred to herein as mono, di or trialkoxysilanes, are those that are capable of being functionalized with NO. Prior to functionalizing with NO, the monoalkoxysilanes are selected from the group consisting of N-(2-aminoethyl)-3-amino-isobutyl-dimethylmethoxysilane (AEAI); aminopropyldimethylethoxysilane (APDE); N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl)phenethyltrimethoxysilane (AEMP3); [3-(methylamino)propyl]trimethoxysilane (MAP3); N-butylamino-propyltrimethoxysilane (n-BAP3); t-butylaminopropyltrimethoxysilane(t-BAP3); N-ethylaminoisobutyltrimethoxysilane (EAiB3); N-phenylaminopropyltrimethoxysilane (PAP3); and N-cyclohexylaminopropyltrimethoxysilane (cHAP3).

Any suitable diazeniumdiolate-modified alkoxysilane, or mixtures thereof, may be included. In some embodiments, the diazeniumdiolate-modified alkoxysilane may include a diazeniumdiolate-modified alkoxysilane having the formula of R''—N(NONO$^-$X$^+$)—R'—Si(OR)$_3$, wherein each R is independently H, alkyl or substituted alkyl; R' is substituted or unsubstituted alkylene, substituted or unsubstituted arylene, substituted or unsubstituted alkylarylene or substituted or unsubstituted arylalkylene; R'' is H, alkyl or substituted alkyl; and X$^+$ is a monovalent cation such as Na$^+$, K$^+$, Cs$^+$, or Li$^+$, a divalent cation, or a cationic amine. The diazeniumdiolate-modified alkoxysilane may prepared by any suitable method. However, methods of synthesizing diazeniumdiolate-modified alkoxysilanes are described in U.S. Patent Application Publication No. 2009/0214618 to Schoenfisch et al., which is hereby incorporated by reference herein in its entirety.

As an example, a diazeniumdiolate-modified alkoxysilane may be prepared by exposing an appropriate aminoalkoxysilane to NO gas (e.g., between 1 and 34 atm) in a solution, such as a solution that includes sodium methoxide and a methanol co-solvent. In some embodiments the ratio of sodium methoxide to aminoalkoxysilane ranges from 0.8:1 to 1.25:1 to maximize the conversion of the amines to diazeniumdiolate NO donors. In such cases, any suitable aminoalkoxysilane may be used. However, in some embodiments, the aminoalkoxysilane may include a primary amine such as 3-aminopropyltrimethoxysilane (APTMS); 3-aminopropyltriethoxysilane (APTES); 4-aminobutyltriethoxysilane (ABTES); 4-amino-3,3-dimethylbutyltrimethoxysilane (ADBTMS); a secondary amine such as [3-(methylamino)propyl]trimethoxysilane (MAP3); N-butylamino-propyltrimethoxysilane (n-BAP3); t-butylamino-propyltrimethoxysilane (t-BAP3); 3-(N-styrylmethyl-2-aminoethylamino)-propyltrimethoxysilane (SEAP3); N-ethylaminoisobutyltrimethoxysilane (EAiB3); N-phenylamino-propyltrimethoxysilane (PAP3); and N-cyclohexylaminomethyltrimethoxysilane (cHAM3); N-cyclohexylaminopropyltrimethoxysilane (cHAP3); diamines such as (aminoethylaminomethyl)phenethyltrimethoxysilane (AEMP3); N-(6-aminohexyl)aminopropyltrimethoxysilane (AHAP3); N-(6-aminohexyl)aminomethyltriethoxysilane) (AHAM3); N-(2-aminoethyl)-3-aminopropyltrimethoxysilane (AEAP3); N-(2-aminoethyl)-11-aminoundecyltrimethoxysilane (AEAUD3); (2-N-benzylaminoethyl)-3-aminopropyltrimethoxysilane (BEAP3); and/or polyamines such as (3-trimethoxysilylpropyl)diethylenetriamine (DET3). Other aminoalkoxysilanes that may be used in some embodiments include 3-aminopropyldimethoxysilane, N-(3-acryloxy-2-hydroxypropyl)-3-aminopropyltriethoxysilane, N-2-(aminoethyl)-3-aminopropyltris(2-ethyl-hexyloxy)silane, 3-(m-aminophenoxy)propyltrimethoxysilane, 3-(1-aminopropoxy)-3,3-dimethyl-1-propenyltrimethyoxysilane, 3-aminopropyltris(methoxyethoxyethoxy)silane, 3-aminopropylmethyldiethoxysilane, 3-aminopropyltris(trimethylsiloxy)silane, bis(dimethylamino)methylmethoxysilane, bis(dimethylamino)phenylethoxysilane, bis(2-hydroxyethyl)-3-aminopropyltriethoxysilane, bis(2-hydroxyethyl)-3-aminopropyltrimethoxysilane, bis(3-triethoxysilyl)propylamine, 1,4-bis[3-(trimethoxysilyl)propyl]ethylenediamine, (N,N-diethyl-3-aminopropyl)trimethoxysilane, (N,N-dimethyl-3-aminopropyl)trimethoxysilane, N-phenylaminopropyltrimethoxysilane, trimethoxysilylpropyldiethylenetriamine, trimethoxysilylpropylpentaethylenehexamine, triethoxysilyloctyldiethylenetriamine, triisopropoxysilylpentaethylenehexamine, 3-aminopropylmethyldiethoxysilane, 2-(perfluorooctyl) ethyltriaminotrimethoxysilane, 4-aminobutyltrimethoxysilane, N-(6-aminohexyl)aminopropyltrimethoxysilane, 3-(dimethoxymethylsilylpropyl)diethylenetriamine, N-(2-aminoethyl)-N'-[3-(dimethoxymethylsilyl)propyl]-1,2-ethanediamine and amine-modified polydimethylsiloxane copolymer (available from Dow Corning as "MDX4-4159").

In some embodiments, the aminoalkoxysilane may have the formula: NH [R'—Si(OR)$_3$]$_2$, wherein R is H, alkyl or substituted alkyl and R' is substituted or unsubstituted alkylene, substituted or unsubstituted arylene, substituted or unsubstituted alkylarylene or substituted or unsubstituted arylalkylene. In some embodiments, the diazeniumdiolate modified alkoxysilane may include a dipodal aminoalkoxysilane such as bis-(trimethoxysilylpropyl)amine, bis-(triethoxysilylpropyl)amine, bis-(triethoxysilylpropyl)ethylene diamine, N-[2-vinylbenzylamino)ethyl]-3-aminopropyltrimethoxysilane, aminoethylaminopropyltrimethoxysilane, trimethoxysilyl-modified polyethylenimine, methyldimethoxysilyl-modified polyethylenimine, bis-[(3-trimethoxysilyl)propyl]ethylenediamine, bis(methyldiethoxysilylpropyl)amine, bis(triethoxysilylmethyl)amine, N,N'-bis[(3-trimethoxysilyl)propyl]ethylenediamine.

In some embodiments of the invention, the diazeniumdiolate-modified alkoxysilane may be $O^2$-protected prior to the preparation of sol-gel coatings. Such $O^2$-protected diazeniumdiolate modified aminoalkoxysilanes may have the formula: R"—N(NONO—R''')—R'—Si(OR)$_3$, wherein each R is independently H, alkyl or substituted alkyl, R' is substituted or unsubstituted alkylene, substituted or unsubstituted arylene, substituted or unsubstituted alkylarylene or substituted or unsubstituted arylalkylene, R" is H, alkyl or substituted alkyl and R''' is a protecting group that imparts pH dependent, enzymatic, photolytic, or thiolation triggering mechanisms. Such protecting groups are known to those skilled in the art of forming $O^2$-protected diazeniudiolates.

Useful aspect ratios of the nitric oxide-releasing nanorods have a value of at least about 1. Other useful values of aspect ratios include 2, 3, 4, 5, 6, 7, 8, 9, 10, 11, 12, 13, 14, 15, 16, 17, 18, 19 and 20 or more. Preferably, the aspect ratio is about 4. Also preferred are aspect ratios of from about 6 to about 10. Most preferably, the aspect ratio is about 8. The aspect ratio can be determined as described herein or can be determined by other techniques known in the art.

The nitric oxide-releasing nanorods have an initial NO flux. This is described herein as $[NO]_{max}$ and can be measured by a nitric oxide analyzer as is known in this field. Useful values of $[NO]_{max}$ are from about 10 to about 16,000 ppb/mg; from about 10 to about 14,000 ppb/mg; from about 10 to about 12,000 ppb/mg; from about 10 to about 10,000 ppb/mg; from about 10 to about 8,000 ppb/mg; from about 10 to about 6,000 ppb/mg; from about 10 to about 4,000 ppb/mg; from about 10 to about 2,000 ppb/mg; from about 10 to about 1,000 ppb/mg; and from about 10 to about 500 ppb/mg. Other useful values are above 3,000 ppb/mg. Preferably, the value is from about 3,000 ppb/mg to about 16,000 ppb/mg. More preferably, the value is from about 3,000 ppb/mg to about 7,000 ppb/mg. Most preferably, the value is about 5,000 ppb/mg.

The nanorods may have a length that is measured as about 1,700 nm or less. Preferably, the nanorod has a length of from about 100 nm to about 1,300 nm. More preferably, the nanorod has a length of from about 500 nm to about 1,600 nm. Most preferably, the nanorod has a length of from about 1,000 nm to about 1,200 nm. In an embodiment, the nanorods further comprise a polymer or small molecule agent that is covalently attached to at least one of the mono, di or trialkoxysilane moieties that is on the surface of the nanorod. Agents can be epoxide, acrylate or N-hydroxysuccinimide esters. Preferably, the polymer is a polyethylene glycol (PEG) polymer. PEG has the structure: —(CH$_2$CH$_2$O)$_x$—, wherein x is an integer from one to 10,000. Preferred values of x are integers from one to 500. More preferred values of x are integers from one to 200. Also more preferred values of x are integers from one to 50. The most preferred values of x are integers from one to 10.

The nitric oxide-releasing nanorods comprise a NO donor. The NO donor is covalently attached to the mono, di or trialkoxysilane residue that is pendant on the nanorod. The NO donor is selected from the group consisting of a diazeniumdiolate, nitrosothiol, a nitrosamine, a hydroxyl nitrosamine, a hydroxylamine, a hydroxyurea, and combination thereof. Preferably, the NO donor is a diazeniumdiolate.

Nitric oxide-releasing (e.g., silica mesoporous) nanorods have been synthesized. As disclosed herein, the aspect ratios (ARs) of the rods can be controlled by varying the temperature and the concentration of ammonia and silane.

In an embodiment, the subject matter described herein is directed to a method of preparing a nitric oxide-releasing nanorod, comprising:

a. contacting a silane with ammonia, sodium acetate, potassium acetate, sodium hydroxide or potassium hydroxide and mixtures thereof in the presence of a surfactant at a temperature $T_1$; to form a first composition;
b. allowing the first composition to age for a period of time, P, at a temperature $T_2$ to form a nanorod;
c. harvesting the nanorod;
d. contacting the harvested nanorod with a mono, di or trialkylsilane at a temperature, $T_3$, to form a amine-functionalized nanorod;
e. harvesting the amine-functionalized nanorod;
f. contacting the harvested amine-functionalized nanorod with NO gas to form a nitric-oxide releasing nanorod; and
g. harvesting the nitric-oxide releasing nanorod.

Each of these procedures is described fully elsewhere herein. As described herein, a functionalized nanorod comprising a silane and a functionalized mono, di or trialkoxysilane refers to a nanorod that has been prepared as described herein from a silane and its surfaces have been functionalized with the mono, di or trialokysilanes. The mono, di or trialkoxysilanes can be covalently linked to the silane nanorod through silanol groups on the surfaces of the nanorod.

Useful surfactants include a quaternary ammonium surfactant (C$_n$H$_{n+1}$(CH$_3$)$_3$N$^+$X, wherein X is Cl or Br and n is an integer from 8 to 16; non-ionic alkyl poly(ethylene oxide) (PEO) oligomeric surfactants; and poly-(alkylene oxide) triblock copolymers. Preferably, the surfactant is cetylammonium bromide.

The time period, P, includes 5-30 minutes, 30 minutes-1 hour, 1-12 hours, 12-24 hours, days or weeks.

The temperatures $T_1$, $T_2$ and $T_3$ are each independent. Temperature $T_1$ is from about 20° C. to about 200° C. Preferably, $T_1$ is from about 30° C. to 70° C. Temperature $T_2$ is from about 20° C. to about 200° C. Preferably, $T_2$ is from about 30° C. to 70° C. Step d is preferably performed under reflux conditions. Temperature $T_3$ is from about 50° C. to 300° C. Preferably, $T_3$ is from about 60° C. to about 200° C. More preferably, $T_3$ is from about 60° C. to 120° C.

As used herein, the term "harvesting" includes filtration, centrifugation, separation and the like. In addition to these methods of harvesting, the method can include washing the nanorods after harvesting.

In an embodiment, the subject matter disclosed herein is directed to a composition comprising, a nanorod, wherein said nanorod comprises a silane and a functionalized mono, di or trialkoxysilane, wherein said functionalized mono, di or trialkoxysilane is covalently bound to a NO-donor molecule; wherein said nanorods have an aspect ratio of at least 1 and a $[NO]_{max}$ of at least 10 ppb/mg. Preferably, the composition comprises a plurality of nanorods, wherein said nanorods have an aspect ratio of from about 1 to about 10 and a $[NO]_{max}$ of from about 10 to about 16,0000 ppb/mg. More preferably, the composition comprises a plurality of nanorods, wherein said nanorods have an aspect ratio of from about 4 to about 10 and a $[NO]_{max}$ of from about 3,000 ppb/mg to about 7,000 ppb/mg. The compositions may contain a monodisperse plurality.

The compositions described herein include pharmaceutical formulations. Thus, in yet another embodiment, the subject matter disclosed herein is directed to a pharmaceutical formulation comprising a nitric oxide-releasing nanorod and a pharmaceutically acceptable excipient, diluent or carrier.

The nanorods disclosed herein are effective at treating bacteria. Preferably, the nanorods or compositions comprising the nanorods have an MBC below about 250 µg/mL. More preferably, the compositions have an MBC below about 200 µg/mL. Most preferably, the compositions have a MBC below about 150 µg/mL.

The shape of a nanorod plays a role in the in vivo effects produced by the nanorods. Properties affected by the shape of the nanorod are strength of adhesion to cells, targeting ability, internalization rate at the cellular level, transport in the body and circulation time, i.e., resistance to phagocytosis.

The bactericidal activity of NO-releasing silica nanorods against Gram-negative (*P. aeruginosa*) and -positive (*S. aureus*) bacteria appear to depend on both the NO flux and nanorod morphology. For example, we have found that significantly less NO is required to kill bacteria from NO-releasing silica nanorods with higher aspect ratio or greater NO flux due to more efficient NO delivery to the bacterium. Regardless of morphology or NO flux, the NO-releasing silica nanorods were nontoxic to L929 mouse fibroblast cells at bactericidal concentration against *P. aeruginosa*.

At an aspect ratio of about 8, the NO-releasing SNRs described herein eradicated *S. aureus* at non-cytotoxic concentrations to L929 fibroblasts, demonstrating the variance in bactericidal efficacy and toxicity. Of note, effective killing was nevertheless achievable at nontoxic (mammalian cells) concentration. In particular, the nanorods described herein can be used to combat biofilms.

In another embodiment, the subject matter disclosed herein is directed to a method of disrupting, eradicating or preventing a biofilm. This method comprises subjecting a biofilm to a NO-releasing nanorod as disclosed herein. The term "biofilm" is intended to mean an aggregate of one or more microorganisms in which cells adhere to each other, usually on a surface. Most any free-floating microorganisms can form a biofilm and/or attach to a surface. Microorganisms can adhere to a surface or each other through weak, reversible adhesion via van der Waals forces. The microorganisms can more permanently anchor using cell adhesion or structures such as pili. Greater than 99% of all bacteria live in biofilm communities that offer significantly greater protection against antimicrobial agents. (Smith, A. W., Biofilms and antibiotic therapy: Is there a role for combating bacterial resistance by the use of novel drug delivery systems? *Adv. Drug Delivery Rev.* 2005, 57 (10), 1539-1550)

The terms "disrupting" and "eradicating" refer to the ability of the presently disclosed NO-releasing nanorods to combat biofilms. The biofilms may be partially eradicated or disrupted, meaning that the cells no longer attach to one another or to a surface. The biofilm may be completely eradicated, meaning that the biofilm is no longer an interconnected, cohesive or continuous network of cells to a substantial degree.

In an embodiment, the subject matter described herein is directed to a method of delivering nitric oxide to a subject, comprising administering an effective amount of a nitric oxide-releasing nanorod to a subject.

In an embodiment, the subject matter described herein is directed to a method of treating a bacterial infection in a subject, comprising administering an effective amount of a nitric oxide-releasing nanorod to a subject in need thereof. In this embodiment, the bacteria can be a gram-negative or positive bacterium. In an aspect of this embodiment, the bacteria are selected from the group consisting of *P. aeruginosa, S. aureus, E. faecalis*, VREF, *S. epidermis*, MRSA, *E. coli, P. mirabilis* and *S. mutans*. In a particularly useful embodiment, the bacteria are selected from the group consisting of *P. aeruginosa* and *S. aureus*.

Routes of administration for a therapeutically effective amount of a nitric oxide-releasing nanorod include but are not limited to intravenous or parenteral administration, oral administration, topical administration, transmucosal administration and transdermal administration. For intravenous or parenteral administration, i.e., injection or infusion, the composition may also contain suitable pharmaceutical diluents and carriers, such as water, saline, dextrose solutions, fructose solutions, ethanol, or oils of animal, vegetative, or synthetic origin. It may also contain preservatives, and buffers as are known in the art. When a therapeutically effective amount is administered by intravenous, cutaneous or subcutaneous injection, the solution can also contain components to adjust pH, isotonicity, stability, and the like, all of which is within the skill in the art. The pharmaceutical composition of the present invention may also contain stabilizers, preservatives, buffers, antioxidants, or other additive known to those of skill in the art. Typically, compositions for intravenous or parenteral administration comprise a suitable sterile solvent, which may be an isotonic aqueous buffer or pharmaceutically acceptable organic solvent. The compositions can also include a solubilizing agent as is known in the art if necessary. Compositions for intravenous or parenteral administration can optionally include a local anesthetic to lessen pain at the site of the injection. Generally, the ingredients are supplied either separately or mixed together in unit dosage form in a hermetically sealed container such as an ampoule or sachette. The pharmaceutical compositions for administration by injection or infusion can be dispensed, for example, with an infusion bottle containing, for example, sterile pharmaceutical grade water or saline. Where the pharmaceutical compositions are administered by injection, an ampoule of sterile water for injection, saline, or other solvent such as a pharmaceutically acceptable organic solvent can be provided so that the ingredients can be mixed prior to administration.

The duration of intravenous therapy using the pharmaceutical composition comprising a nitric oxide-releasing nanorod will vary, depending on the condition being treated or ameliorated and the condition and potential idiosyncratic response of each individual mammal. The infusion can be repeated as necessary.

Systemic formulations include those designed for administration by injection, e.g., subcutaneous, intravenous, intramuscular, intrathecal or intraperitoneal injection. Useful injectable preparations include sterile suspensions, solutions or emulsions of the active compound(s) in aqueous or oily vehicles. The compositions also can contain solubilizing agents, formulating agents, such as suspending, stabilizing and/or dispersing agent. The formulations for injection can be presented in unit dosage form, e.g., in ampules or in multidose containers, and can contain added preservatives. For prophylactic administration, the compound can be administered to a patient at risk of developing one of the previously described conditions or diseases. Alternatively, prophylactic administration can be applied to avoid the onset of symptoms in a patient suffering from or formally diagnosed with the underlying condition.

The amount of a nitric oxide-releasing nanorod administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art coupled with the general and specific examples disclosed herein.

Oral administration of the composition or vehicle can be accomplished using dosage forms including but not limited to capsules, caplets, solutions, suspensions and/or syrups. Such dosage forms are prepared using conventional methods known to those in the field of pharmaceutical formulation and described in the pertinent texts, e.g., in *Remington: The Science and Practice of Pharmacy* (2000), supra.

The dosage form may be a capsule, in which case the active agent-containing composition may be encapsulated in the form of a liquid. Suitable capsules may be either hard or soft, and are generally made of gelatin, starch, or a cellulosic material, with gelatin capsules preferred. Two-piece hard gelatin capsules are preferably sealed, such as with gelatin bands or the like. See, for e.g., *Remington: The Science and Practice of Pharmacy* (2000), supra, which describes materials and methods for preparing encapsulated pharmaceuticals.

Capsules may, if desired, be coated so as to provide for delayed release. Dosage forms with delayed release coatings may be manufactured using standard coating procedures and equipment. Such procedures are known to those skilled in the art and described in the pertinent texts (see, for e.g., *Remington: The Science and Practice of Pharmacy* (2000), supra). Generally, after preparation of the capsule, a delayed release coating composition is applied using a coating pan, an airless spray technique, fluidized bed coating equipment, or the like. Delayed release coating compositions comprise a polymeric material, e.g., cellulose butyrate phthalate, cellulose hydrogen phthalate, cellulose proprionate phthalate, polyvinyl acetate phthalate, cellulose acetate phthalate, cellulose acetate trimellitate, hydroxypropyl methylcellulose phthalate, hydroxypropyl methylcellulose acetate, dioxypropyl methylcellulose succinate, carboxymethyl ethylcellulose, hydroxypropyl methylcellulose acetate succinate, polymers and copolymers formed from acrylic acid, methacrylic acid, and/or esters thereof.

Sustained-release dosage forms provide for drug release over an extended time period, and may or may not be delayed release. Generally, as will be appreciated by those of ordinary skill in the art, sustained-release dosage forms are formulated by dispersing a drug within a matrix of a gradually bioerodible (hydrolyzable) material such as an insoluble plastic, a hydrophilic polymer, or a fatty compound. Insoluble plastic matrices may be comprised of, for example, polyvinyl chloride or polyethylene. Hydrophilic polymers useful for providing a sustained release coating or matrix cellulosic polymers include, without limitation: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS) preferred; vinyl polymers and copolymers such as polyvinyl pyrrolidone, polyvinyl acetate, polyvinylacetate phthalate, vinylacetate crotonic acid copolymer, and ethylene-vinyl acetate copolymers; zein; and shellac, ammoniated shellac, shellac-acetyl alcohol, and shellac n-butyl stearate. Fatty compounds for use as a sustained release matrix material include, but are not limited to, waxes generally (e.g., carnauba wax) and glyceryl tristearate.

Topical administration of an agent containing a nitric oxide-releasing nanorod can be accomplished using any formulation suitable for application to the body surface, and may comprise, for example, an ointment, cream, gel, lotion, solution, paste or the like, and/or may be prepared so as to contain liposomes, micelles, and/or microspheres. Preferred topical formulations herein are ointments, creams, and gels.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in *Remington: The Science and Practice of Pharmacy* (2000), supra, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight (See, e.g., *Remington: The Science and Practice of Pharmacy* (2002), supra).

Creams, as also well known in the art, are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

As will be appreciated by those working in the field of pharmaceutical formulation, gels—are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are crosslinked acrylic acid polymers such as the "carbomer" family of polymers, e.g., carboxypolyalkylenes that may be obtained commercially under the Carbopol® trademark. Also preferred are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methylcellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

Various additives, known to those skilled in the art, may be included in the topical formulations. For example, solubilizers may be used to solubilize certain active agents. For those drugs having an unusually low rate of permeation through the skin or mucosal tissue, it may be desirable to include a permeation enhancer in the formulation; suitable enhancers are as described elsewhere herein.

The dosage unit will generally contain from about 0.1 wt. % to about 60 wt. % nitric oxide-releasing nanorods, preferably on the order of from about 1 wt. % to about 30 wt. % active agent.

The composition can include a bioerodible (hydrolyzable) polymeric carrier. It will be appreciated that virtually any such carrier can be used, so long as the desired drug release profile is not compromised, and the carrier is compatible with a nitric oxide-releasing nanorod.

Generally, the polymeric carrier comprises a hydrophilic (water-soluble and water-swellable) polymer that adheres to the wet surface of the buccal mucosa. Examples of polymeric carriers useful herein include acrylic acid polymers and co, e.g., those known as "carbomers" (Carbopol®, which may be obtained from B. F. Goodrich, is one such polymer). Other suitable polymers include, but are not limited to: hydrolyzed polyvinylalcohol; polyethylene oxides (e.g., Sentry Polyox® water soluble resins, available from Union Carbide); polyacrylates (e.g., Gantrez®, which may be obtained from GAF); vinyl polymers and copolymers; polyvinylpyrrolidone; dextran; guar gum; pectins; starches; and cellulosic polymers such as hydroxypropyl methylcellulose, (e.g., Methocel®, which may be obtained from the Dow Chemical Company), hydroxypropyl cellulose (e.g., Klucel®, which may also be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated. The additional components include, but are not limited to, disintegrants, diluents, binders, lubricants, flavoring, colorants, preservatives, and the like. Examples of disintegrants that may be used include, but are not limited to, cross-linked polyvinylpyrrolidones, such as crospovidone (e.g., Polyplasdone® XL, which may be obtained from GAF), cross-linked carboxylic methylcelluloses, such as croscarmelose (e.g., Ac-disol®, which may be obtained from FMC), alginic acid, and sodium carboxymethyl starches (e.g., Explotab®, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pak®, which may be obtained from Amstar), calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Particularly preferred lubricants are stearates and stearic acid, and an optimal lubricant is magnesium stearate.

Dosage forms also include creams, ointments and pastes. The cream, ointment or paste comprises a therapeutically effective amount of a nitric oxide-releasing nanorod and one or more conventional nontoxic carriers.

Other components may also be incorporated into the formulations. The additional components include, but are not limited to binders, disintegrants, wetting agents, lubricants, and the like. Examples of binders that may be used include water, ethanol, polyvinylpyrrolidone; starch solution gelatin solution, and the like. Suitable disintegrants include dry starch, calcium carbonate, polyoxyethylene sorbitan fatty acid esters, sodium lauryl sulfate, stearic monoglyceride, lactose, and the like. Wetting agents, if used, include glycerin, starches, and the like. Particularly preferred lubricants are stearates and polyethylene glycol. Additional components that may be incorporated into sublingual and lingual dosage forms are known, or will be apparent, to those skilled in this art (See, e.g., *Remington: The Science and Practice of Pharmacy* (2000), supra).

Transdermal drug delivery may involve delivery through the skin. It may be accomplished through passive diffusion or it may be facilitated using electrotransport, e.g., iontophoresis. In a typical transdermal "patch," the drug composition is contained in a layer, or "reservoir," underlying an upper backing layer. The laminated structure may contain a single reservoir, or it may contain multiple reservoirs. In one type of patch, referred to as a "monolithic" system, the reservoir is comprised of a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are separate and distinct layers, with the adhesive underlying the reservoir which, in this case, may be either a polymeric matrix as described above, or it may be a liquid or hydrogel reservoir, or may take some other form.

Transdermal drug delivery systems may in addition contain a skin permeation enhancer. That is, because the inherent permeability of the skin to some drugs may be too low to allow therapeutic levels of the drug to pass through a reasonably sized area of unbroken skin, it is necessary to coadminister a skin permeation enhancer with such drugs. Suitable enhancers are well known in the art and include, for example, those enhancers listed below in transmucosal compositions.

Formulations can comprise one or more anesthetics. Patient discomfort or phlebitis and the like can be managed using anesthetic at the site of injection. If used, the anesthetic can be administered separately or as a component of the composition. One or more anesthetics, if present in the composition, is selected from the group consisting of lignocaine, bupivacaine, dibucaine, procaine, chloroprocaine, prilocalne, mepivacaine, etidocaine, tetracaine, lidocaine and xylocalne, and salts, derivatives or mixtures thereof.

Actual dosage levels of active ingredients in an active composition of the presently disclosed subject matter can be varied so as to administer an amount of the active compound(s) that is effective to achieve the desired response for a particular subject and/or application. The selected dosage level will depend upon a variety of factors including the activity of the composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of an effective dose, as well as evaluation of when and how to make such adjustments, are known to those of ordinary skill in the art of medicine.

For administration of a composition as disclosed herein, conventional methods of extrapolating human dosage based on doses administered to a murine animal model can be carried out using the conversion factor for converting the mouse dosage to human dosage: Dose Human per kg=Dose Mouse per kg×12. See Freireich et al., *Cancer Chemother Rep.* 50, 219-244 (1966). Drug doses also can be given in milligrams per square meter of body surface area because this method rather than body weight achieves a good correlation to certain metabolic and excretionary functions. Moreover, body surface area can be used as a common denominator for drug dosage in adults and children as well as in different animal species. See Freireich et al., *Cancer Chemother Rep.* 50, 219-244 (1966). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

For additional guidance regarding formulation and dose, see U.S. Pat. Nos. 5,326,902; 5,234,933; PCT International Publication No. WO 93/25521; Berkow et al., *The Merck Manual of Medical Information*, Home ed., Merck Research Laboratories: Whitehouse Station, N.J. (1997); Goodman et al., *Goodman & Gilman's the Pharmacological Basis of Therapeutics*, 9th ed. McGraw-Hill Health Professions Division: New York (1996); Ebadi, *CRC Desk Reference of Clinical Pharmacology*, CRC Press, Boca Raton, Fla. (1998); Katzunq, *Basic & Clinical Pharmacology*, 8th ed. Lange Medical Books/McGraw-Hill Medical Pub. Division: New York (2001); Remington et al., *Remington's Pharmaceutical Sciences*, 15th ed. Mack Pub. Co.: Easton, Pa. (1975); and Speight et al., *Avery's Drug Treatment: A Guide to the Properties, Choice, Therapeutic Use and Economic Value of Drugs in Disease Management*, 4th ed. Adis International: Auckland/Philadelphia (1997); Dutch et al., *Toxicol. Leu.*, 100-101, 255-263 (1998).

Suitable methods for administering to a subject a composition of the presently disclosed subject matter include, but are not limited to, systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

The particular mode of drug administration used in accordance with the methods of the presently disclosed subject matter depends on various factors, including but not limited to the agent and/or carrier employed, the severity of the condition to be treated, and mechanisms for metabolism or removal of the active agent following administration.

In some embodiments, one or more additional therapeutic agents can be used in combination with NO-releasing nanorod. Such additional agents can be part of a formulation comprising the NO-releasing nanorod or dosed as a separate formulation prior to, after, or at the same time (concurrently) as a formulation including the NO-releasing nanorod. Such additional therapeutic agents include, in particular, anti-cancer therapeutics, anti-microbial agents, pain relievers, anti-inflammatories, vasodialators, and immune-suppresants, as well as any other known therapeutic agent that could enhance the alleviation of the disease or condition being treated. "Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The choice of additional therapeutic agents to be used in combination with a NO-releasing nanorod will depend on various factors including, but not limited to, the type of disease, the age, and the general health of the subject, the aggressiveness of disease progression, and the ability of the subject to tolerate the agents that comprise the combination.

A variety of chemical compounds, also described as "antineoplastic" agents or "chemotherapeutic agents" can be used in combination with the presently disclosed NO-releasing nanorods used in the treatment of cancer. Such chemotherapeutic compounds include, but are not limited to, alkylating agents, DNA intercalators, protein synthesis inhibitors, inhibitors of DNA or RNA synthesis, DNA base analogs, topoisomerase inhibitors, anti-angiogenesis agents, and telomerase inhibitors or telomeric DNA binding compounds. For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, including alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents, such as distamycin and netropsin, can be used as part of the presently disclosed cancer treatments. Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, a-amanitine and other fungal amatoxins, cordycepin (3'-deoxyadenosine), dichlororibofuranosyl benzimidazole, rifampicine, streptovaricin, and streptolydigin also can be combined with NO-releasing nanorods to provide a suitable cancer treatment.

Thus, current chemotherapeutic agents that can be used in combination with the presently described NO-releasing nanorods include, adrimycin, 5-fluorouracil (5FU), etoposide, camptothecin, actinomycin-D, mitomycin, cisplatin, hydrogen peroxide, carboplatin, procarbazine, mechlorethamine, cyclophosphamide, ifosfamide, melphalan, chlorambucil, bisulfan, nitrosurea, dactinomycin, duanorubicin, doxorubicin, bleomycin, pilcomycin, tamoxifen, taxol, transplatimun, vinblastin, and methotrexate, and the like.

As used herein, the term "antimicrobial agent" refers to any agent that kills, inhibits the growth of, or prevents the growth of a bacteria, fungus, yeast, or virus. Suitable antimicrobial agents that can be incorporated into the presently disclosed NO-releasing nanorods to aid in the treatment or prevention of a microbial infection, include, but are not limited to, antibiotics such as vancomycin, bleomycin, pentostatin, mitoxantrone, mitomycin, dactinomycin, plicamycin and amikacin. Other antimicrobial agents include antibacterial agents such as 2-p-sulfanilyanilinoethanol, 4,4'-sulfinyldianiline, 4-sulfanilamidosalicylic acid, acediasulfone, acetosulfone, amikacin, amoxicillin, amphotericin B, ampicillin, apalcillin, apicycline, apramycin, arbekacin, aspoxicillin, azidamfenicol, azithromycin, aztreonam, bacitracin, bambermycin(s), biapenem, brodimoprim, butirosin, capreomycin, carbenicillin, carbomycin, carumonam, cefadroxil, cefamandole, cefatrizine, cefbuperazone, cefclidin, cefdinir, cefditoren, cefepime, cefetamet, cefixime, cefinenoxime, cefininox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, chloramphenicol, chlortetracycline, ciprofloxacin, clarithromycin, clinafloxacin, clindamycin, clindamycin phosphate, clomocycline, colistin, cyclacillin, dapsone, demecicycline, diathymosulfone, dibekacin, dihydrostreptomycin, dirithromycin, doxycycline, enoxacin, enviomycin, epicillin, erythromycin, flomoxef, fortimicin(s), gentamicin(s), glucosulfone solasulfone, gramicidin S, gramicidin(s), grepafloxacin, guamecycline, hetacillin, imipenem, isepamicin, josamycin, kanamycin(s), leucomycin(s), lincomycin, lomefloxacin, lucensomycin, lymecycline, meclocycline, meropenem, methacycline, micronomicin, midecamycin(s), minocycline, moxalactam, mupirocin, nadifloxacin, natamycin, neomycin, netilmicin, norfloxacin, oleandomycin, oxytetracycline, p-sulfanilylbenzylamine, panipenem, paromomycin, pazufloxacin, penicillin N, pipacycline, pipemidic acid, polymyxin, primycin, quinacillin, ribostamycin, rifamide, rifampin, rifamycin SV, rifapentine, rifaximin, ristocetin, ritipenem, rokitamycin, rolitetracycline, rosaramycin, roxithromycin, salazosulfadimidine, sancycline, sisomicin, sparfloxacin, spectinomycin, spiramycin, streptomycin, succisulfone, sulfachrysoidine, sulfaloxic acid, sulfamidochrysoidine, sulfanilic acid, sulfoxone, teicoplanin, temafloxacin, temocillin, tetracycline, tetroxoprim, thiamphenicol, thiazolsulfone, thiostrepton, ticarcillin, tigemonam, tobramycin, tosufloxacin, trimethoprim, trospectomycin, trovafloxacin, tuberactinomycin and vancomycin. Antimicrobial agents can also include anti-fungals, such as amphotericin B, azaserine, candicidin(s), chlorphenesin, dermostatin(s), filipin, fungichromin, mepartricin, nystatin, oligomycin(s), perimycin A, tubercidin, imidazoles, triazoles, and griesofulvin.

In some embodiments, the NO-releasing nanorod can be incorporated into polymeric films. Such incorporation can be through physically embedding the nanorods into polymer surfaces, via electrostatic association of the nanorods onto polymeric surfaces, or by covalent attachment of NO-releasing nanorods onto reactive groups on the surface of a polymer. Alternatively, the NO-releasing nanorod can be mixed into a solution of liquid polymer precursor, becoming entrapped in the polymer matrix when the polymer is cured. Polymerizable groups can also be used to further functionalize the NO-releasing nanorods, whereupon, the nanorod can be co-polymerized into a polymer during the polymerization process. Suitable polymers into which the NO-releasing nanorods can be incorporated include polyolefins, such as polystyrene, polypropylene, polyethylene, polytetrafluoroethylene, and polyvinylidene, as well as polyesters, polyethers, polyurethanes, and the like. In particular, polyurethanes can include medically segmented polyurethanes. Medically segmented polyurethanes can also include one or more expander moieties, such as alkylene chains, that add additional length or weight to the polymer. Such polyurethanes are also generally non-toxic. One example of a medically segmented polyurethane is TECOFLEX®.

Polymeric films containing NO-releasing nanorods can be used to coat a variety of articles, particularly surgical tools, biological sensors, and medical implants to prevent platelet adhesion, to prevent bacterial infection, to act as a vasodilator. These articles can be of use in vascular medical devices, urological medical devised, biliary medical devices, gastrointestinal medical devices, medical devices adapted for placement at surgical sites, and medical devices adapted for placement on skin wounds or openings. Thus, the polymers can be used to coat arterial stents, guide wires, catheters, trocar needles, bone anchors, bone screws, protective platings, hip and joint replacements, electrical leads, biosensors, probes, sutures, surgical drapes, wound dressings, and bandages.

In some embodiments, the device being coated can have a metallic surface, such as, for example, stainless steel, nickel, titanium, aluminum, copper, gold, silver, platinum, and combinations thereof. In some embodiments, the films or polymers containing the NO-releasing nanorod can be used to coat non-metallic surfaces, such as glass or fiber (e.g., cloth or paper).

Additionally, polymers containing NO-releasing nanorods can be used to form the devices, themselves. For example, the polymers can be fashioned into storage bags for blood or tissue or as wound dressings.

Surfaces that can be contacted with a NO-releasing nanorod to prevent or disrupt biofilms include those selected from the group consisting of medical devices, plumbing fixtures, condenser coils, optical surfaces, boat hulls and aircrafts. Other non-limiting examples include counter tops, windows, appliances, hard floors, rugs, tubs, showers, mirrors, toilets, bidets, bathroom fixtures, sinks, refrigerators, microwaves, small kitchen appliances, tables, chairs, cabinets, drawers, sofas, love seats, benches, beds, stools, armoires, chests, dressers, display cabinets, clocks, buffets, shades, shutters, entertainment centers, arm rails, lamps, banisters, libraries, cabinets, desks, doors, shelves, couches, carts, pianos, statues and other art, racks, fans, light fixtures, pool tables, ping pong tables, soccer tables, card tables, tools (e.g., hand powered and/or hand held tools, electrical tools, air powered tools, etc.), telephones, radios, televisions, stereo equipment, CD and DVD players, analog and digital sound devices, palm computers, laptop computers, desktop and tower computers, computer monitors, mp3 players, memory storage devices, cameras, camcorders, vehicle surfaces (e.g., windshield; tires; metal, fiberglass, composite material and/or plastic outer surfaces; fabric and/or vinyl outer surfaces; fabric, vinyl, and/or leather interior surfaces; metal, plastic, wood and/or composite material interior surfaces, glass interior surfaces, etc.), bicycles, snowmobiles, motorcycles, off-road-vehicles, yard equipment, farm equipment, washing equipment (e.g., power washers, etc.), painting equipment (e.g., electric and air powered painting equipment, etc.), medical and/or dental equipment, marine equipment (e.g., sail boats, power boats, rafts, sail board, canoe, row boats, etc.), toys, writing implements, watches, framed pictures or paintings, books, and/or the like. Any surface where it is desirable to cause one or more types of liquids to run off of a surface, to not be absorbed into a surface, and/or to not stain a surface, can be a substrate. For example, a surface that is exposed to environmental conditions. Also where the surface can become a locus for microbial adhesion such as medical devices that contact bodily tissues or fluids is particularly preferred.

Medical devices such as catheters, which are adapted for movement through blood vessels or other body lumens, are typically provided with low-friction outer surfaces. If the surfaces of the medical devices are not low-friction surfaces, insertion of the devices into and removal of the devices from the body lumens becomes more difficult, and injury or inflammation of bodily tissue may occur. Low friction surfaces are also beneficial for reducing discomfort and injury that may arise as a result of movement between certain long term devices (e.g., long term catheters) and the surrounding tissue, for example, as a result of patient activity. Medical devices include a variety of implantable and insertable medical devices (also referred to herein as "internal medical devices"). Examples of such medical devices include, devices involving the delivery or removal of fluids (e.g., drug containing fluids, pressurized fluids such as inflation fluids, bodily fluids, contrast media, hot or cold media, etc.) as well as devices for insertion into and/or through a wide range of body lumens, including lumens of the cardiovascular system such as the heart, arteries (e.g., coronary, femoral, aorta, iliac, carotid and vertebro-basilar arteries) and veins, lumens of the genitourinary system such as the urethra (including prostatic urethra), bladder, ureters, vagina, uterus, spermatic and fallopian tubes, the nasolacrimal duct, the eustachian tube, lumens of the respiratory tract such as the trachea, bronchi, nasal passages and sinuses, lumens of the gastrointestinal tract such as the esophagus, gut, duodenum, small intestine, large intestine, rectum, biliary and pancreatic duct systems, lumens of the lymphatic system, the major body cavities (peritoneal, pleural, pericardial) and so forth. Non-limiting, specific examples of internal medical devices include vascular devices such as vascular catheters (e.g., balloon catheters), including balloons and inflation tubing for the same, hydrolyser catheters, guide wires, pullback sheaths, filters (e.g., vena cava filters), left ventricular assist devices, total artificial hearts, injection needles, drug delivery tubing, drainage tubing, gastroenteric and colonoscopic tubing, endoscopic devices, endotracheal devices such as airway tubes, devices for the urinary tract such as urinary catheters and ureteral stents, and devices for the neural region such as catheters and wires, trocar needles, bone anchors, bone screws, protective platings, joint replacements, electrical leads, biosensors, probes, sutures, surgical drapes, wound dressings, and bandages. Many devices in accordance with the invention have one or more portions that are cylindrical in shape, including both solid and hollow cylindrical shapes.

Solid substrate materials can include organic materials (e.g., materials containing 50 wt % or more organic species) such as polymeric materials, and inorganic materials (e.g., materials containing 50 wt % or more inorganic species), such as metallic materials (e.g., metals and metal alloys) and non-metallic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others). Specific examples of non-metallic inorganic materials can be materials containing one or more of the following: metal oxides, including aluminum oxides and transition metal oxides (e.g., oxides of titanium, zirconium, hafnium, tantalum, molybdenum, tungsten, rhenium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Further, the NO-releasing nanorod can be incorporated into detergents, such as, but not limited to, anti-microbial soaps. For example, NO-releasing nanorod embedded in bar soaps can be triggered by contact with water and/or a drop in pH upon use. As the outer surface of the bar is eroded or dissolved, additional NO-releasing nanorod within the bar surface become exposed for subsequent uses of the bar. NO-releasing nanorods also can be suspended in liquid soaps. Such soaps or detergents can be used for personal hygiene or to provide anti-microbial treatments for fibers. Such soaps or detergents can also be used to treat household surfaces or any surface in a hospital or other medical environment that may be exposed to microbes such as bacteria, fungi or viruses.

The formulations include all pharmaceutically acceptable salt forms thereof. Examples of such salts include those derived from pharmaceutically acceptable inorganic and organic acids and bases. Examples of suitable acid salts include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts.

Salts derived from appropriate bases include, without limitation, alkali metal (e.g., sodium, potassium), alkaline earth metal (e.g., magnesium and calcium), ammonium and N-(alkyl)$_4^+$ salts.

The NO-releasing nanorods also include those having quaternization of any basic nitrogen-containing group therein.

Tunable Properties of NO-Releasing Nanorods

As shown in FIG. 1 and Table 1, the observed nanorod morphology revealed a positive correlation between reaction temperature and SNR aspect ratio (AR). For example, synthesis at 20° C. yielded nanorods with an AR of ~4.5 (SNR A) while 30 and 50° C. resulted in nanorods with increased AR of ~8.0 (SNR B) and ~9.4 (SNR C), respectively. Temperature also proved to affect the morphology of the SNRs. In contrast to SNR A and B, SNR C exhibited more twisted and curved morphology that may be attributed to defects in the liquid crystal seeds. (Yang, H.; Ozin, G. A.; Kresge, C. T., The role of defects in the formation of mesoporous silica fibers, films, and curved shapes. *Adv. Mater.* 1998, 10, 883-887) The thermal energy available at increased reaction temperature likely allows for greater defect stabilization in the liquid crystal, leading to the formation of twisted and curved silica rods.

As disclosed herein, the aspect ratio of the silica rods are tunable via reaction temperature. The aspect ratio of the resulting nanorods was large (e.g., >4) for silane and ammonia concentrations of 64.0 mM and 0.5 M, respectively. The role of pH and total silane concentration on nanorod morphology is also disclosed herein.

The influence of electrostatic interactions between the surfactant molecules and the silica species on silica rod formation has been reported, (Hayakawa, K.; Kwak, J. C. T. *Cationic Surfactants. In: Surfactant Science Series*; Gorddard, E. D., Ananthapadmanabham, K. P., Eds.; Marcel Dekker: New York, 1991; pp 189-248) As disclosed herein, it was hypothesized that varying the reaction pH would alter rod morphology. The use of higher levels of ammonia (1 M) resulted in SNRs with an aspect ratio of ~1.23 (SNR D). While not being bound to theory, it is thought that this may be attributable to the cooperative assembly of surfactant and silica species. At high pH, the formation of silica oligomers that vary in degree of polymerization and charge represent more efficient multidentate ligands for the cationic surfactant molecules, and thus result in stronger interaction between the two species. (Hayakawa, 1991) The ensuing multidentate binding contributes to preferential side-to-side growth of liquid crystals and a lower aspect ratio.

Both the size and aspect ratio of SNRs were also adjustable as a function of silane concentration. Decreasing the silane concentration from 64.0 mM (SNR D) to 32.0 mM yielded nanorods (SNR E) of smaller size (~0.02 μm$^3$) and aspect ratio (1.10). A similar trend was also observed between SNR C (aspect ratio of 9.4) and SNR F (aspect ratio of 3.1). Collectively, SNRs of a wide range of aspect ratios (~1-10) and volumes (~0.02 and 0.19 μm$^3$) were synthesized by tuning temperature, pH, and silane concentration. SNRs E, A, and B were employed and the role of aspect ratio on bactericidal activity due to their similar size (e.g., nanorod volume ~0.02 μm$^3$), yet distinct aspect ratios (i.e., 1.1, 4.5, and 8.0) is disclosed herein.

The present subject matter is further described herein by the following non-limiting examples which further illustrate the invention, and are not intended, nor should they be interpreted to, limit the scope of the invention.

EXAMPLES

1. Materials

Tetraethyl orthosilicate (TEOS), N-(2-aminoethyl)-3-amino-isobutyl-dimethylmethoxysilane (AEAI), aminopropyldimethylethoxysilane (APDE) and 3-aminopropyltrimethoxysilane (APTMS) were purchased from Gelest (Morrisville, Pa.). Cetyltrimethylammonium bromide (CTAB) was obtained from Acros Organics (Geel, Belgium). Rhodamine B isothiocyanate (RITC), poly(ethylene glycol) methyl ether acrylate (average $M_n$=480) (PEG), propidium iodide (PI), fetal bovine serum (FBS), Dulbecco's Modified Eagle's Medium (DMEM), phenazine methosulfate (PMS), 3-(4,5-dimethylthiazol-2-yl)-5-(3-carboxymethoxyphenyl)-2-(4-sulfophenyl)-2H-tetrazolium inner salt (MTS), trypsin, phosphate buffered saline (PBS) used for cell culture, and penicillin streptomycin (PS) were purchased from the Aldrich Chemical Company (Milwaukee, Wis.). *Pseudomonas aeruginosa* (ATCC#19143) and *Staphylococcus aureus* (ATCC#29231) were obtained from the American Type Culture Collection (Manassas, Va.). L929 mouse fibroblasts (ATCC #CCL-1) were purchased from the University of North Carolina Tissue Culture Facility (Chapel Hill, N.C.). Distilled water was purified with a Millipore Milli-Q Gradient A-10 water purification system (Bedford, Mass.). 4,5-Diaminofluorescein diacetate (DAF-2 DA) was purchased from Calbiochem (San Diego, Calif.). Common laboratory salts and solvents were purchased from Fisher Scientific (Pittsburgh, Pa.). All materials were used as received without further purification unless noted otherwise.

a. Surfactant-Templated Synthesis of Mesoporous Silica Nanorods.

The silica nanorods (SNRs) were synthesized via a surfactant-templated method and tuning the aspect ratio by varying temperature, ammonia concentration, and solution volume (Table 1). In a representative synthesis, 0.11 mL tetraethyl orthosilicate (TEOS) was added to a solution of 0.29 g cetyltrimethylammonium bromide (CTAB) in 50 mL of 0.5 M ammonia at 50° C. A subsequent addition of TEOS (0.60 mL) was added after 5 h of stirring, followed by aging for 24 h at 50° C. As used herein, the terms "aging," "age" or "aged" refer to allowing a composition to stand, mix, stir, settle, etc. either at room temperature or under heating or cooling and optionally under reduced pressure or added pressure. The

TABLE 1

Influence of reaction temperature, pH, and concentration of silane on the size and aspect ratio of silica nanorods.

| Rod | T (° C.) | TEOS (mM) | CTAB (mM) | Ammonia (M) | Length (nm) | Width (nm) | AR |
|---|---|---|---|---|---|---|---|
| SNR A | 20 | 64.0 | 16.0 | 0.5 | 757 ± 42 | 168 ± 36 | 4.5 ± 0.9 |
| SNR B | 30 | 64.0 | 16.0 | 0.5 | 1120 ± 69 | 140 ± 34 | 8.0 ± 1.0 |
| SNR C | 50 | 64.0 | 16.0 | 0.5 | 1077 ± 105 | 115 ± 15 | 9.4 ± 0.7 |
| SNR D | 20 | 64.0 | 16.0 | 1.0 | 671 ± 102 | 543 ± 106 | 1.2 ± 0.5 |
| SNR E | 20 | 32.0 | 8.0 | 1.0 | 302 ± 35 | 280 ± 26 | 1.1 ± 0.1 |
| SNR F | 50 | 42.7 | 10.7 | 0.5 | 241 ± 32 | 78 ± 6 | 3.1 ± 0.3 | resulting SNRs were collected by centrifugation and washed twice with 50 mL of ethanol, recollected via centrifugation, and dried under vacuum at ambient temperature. To remove the CTAB templates, the SNRs were resuspended in a mixture of ethanol and concentrated HCl (9:1; v/v) and stirred at 60° C. for 24 h. Finally, the nanorods were re-collected by centrifugation and washed twice with ethanol before drying under vacuum at ambient temperature. Complete removal of CTAB was confirmed by CHN elemental analysis.

b. Synthesis of Fluorescently-Labeled Mesoporous Silica Nanorods.

Figure 7:
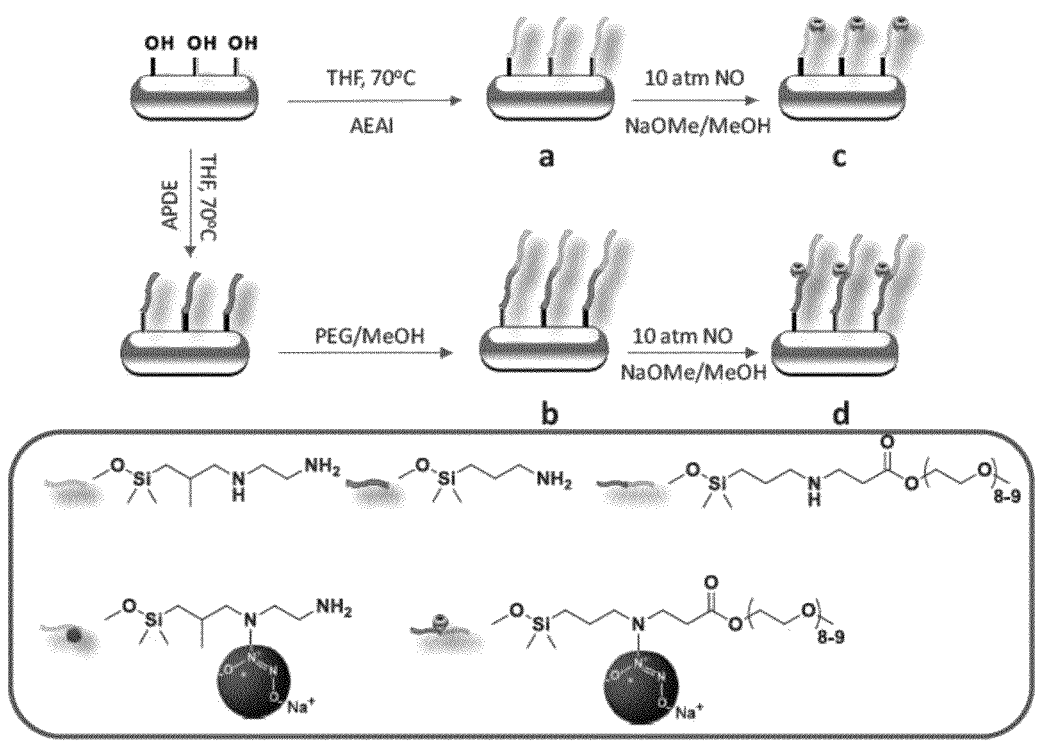
FIG. 7 depicts a synthetic route for preparing certain silica nanorods disclosed herein.
Figure 9:
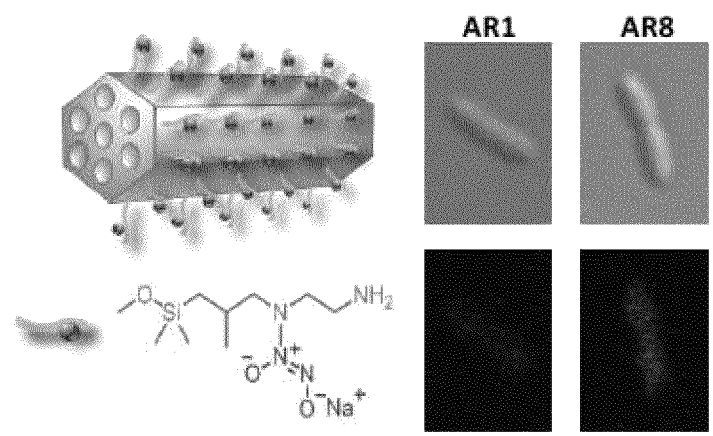
FIG. 9 depicts a representation of the nanorods of certain embodiments, SEMs of AR1 and AR8 and intracellular fluorescence of each.

Rhodamine β isothiocyanate (RITC, 1.52 mg) and 3-aminopropyltrimethoxysilane (ATPMS, 0.5 mL) were dissolved in 0.5 mL ethanol and stirred for 2 d to form RITC-APTMS. A mixture of TEOS and RITC-APTMS (100:1) was used in a typical surfactant-templated synthesis to form RITC modified SNRs. The resulting fluorescently-labeled SNRs were subjected to the same washing and CTAB removal protocols as described above.

c. Preparation of NO-Releasing Mesoporous Silica Nanorods with Functionality c (FIG. 7).

A suspension of 50 mg SNRs and 0.5 mL AEAI in 10 mL anhydrous THF was refluxed under nitrogen overnight. The resulting amine-functionalized SNRs were collected by centrifugation, washed twice with ethanol and dried under vacuum at ambient temperature. Elemental analysis (CHN) was performed to determine the amount of aminoalkoxysilane anchored onto the surface of the SNRs. To modify the SNRs for NO release, 15 mg AEAI-functionalized SNRs (a) were resuspended in a mixture of 2.7 mL anhydrous DMF and 0.3 mL methanol and 50 μL of 5.4M NaOMe/MeOH. The suspension was added to vials in a Pan hydrogenation vessel, purged rapidly (5-10 s) with argon three times, and then three longer cycles (10 min) of argon purges to remove residual oxygen from the solution. The Pan hydrogenation vessel was then filled with 10 atm of NO gas purified over KOH pellets to remove any impurities (NO degradation products) and maintained at 10 atm for 3 d. The same argon purging protocol was performed to remove unbound NO prior to removing the vials from the vessel. The SNRs were recollected by centrifugation, washed twice with anhydrous ethanol, dried under vacuum and stored at −20° C. until future use.

d. Preparation of NO-Releasing Mesoporous Nanosilica Rods with Functionality d (FIG. 7).

Aminopropyldimethylethoxysilane (APDE)-functionalized SNRs were synthesized as described previously for SNRs a by simply replacing AEAI with APDE. Subsequently, poly(ethylene glycol) methyl ether acrylate (PEG) was added to a suspension of APDE-functionalized SNRs in ethanol with equimolar PEG corresponding to the amine content of the SNRs. After stirring at room temperature for 2 d, the PEG-modified SNRs (b) were collected by centrifugation, washed twice with anhydrous ethanol and dried at ambient temperature. The resulting secondary-amine functionalized SNRs b were modified with NO in the same manner described above.

e. Characterization of Functionalized Mesoporous Nanosilica Rods.

Scanning electron micrographs were recorded with a Hitachi S-4700 scanning electron microscope (Pleasanton, Calif.) to determine size and aspect ratios of the SNRs. Elemental (CHN) analysis was performed using a PerkinElmer CHN/S O Elemental Analyzer Series 2400 (Waltham, Mass.) instrument to quantify the amine content of each SNR, that would be proportional to the aminosilane surface coverage. The zeta potential of the silica nanorods was determined using a Zetasizer Nano ZS (Malvern, U. K.), Samples (~1 mg/mL) were prepared in phosphate buffer (10 mM, pH=7.4) and immediately injected into a folded capillary cell for zeta potential analysis. Nitric oxide release was measured using a Sievers 280i Chemiluminesce Nitric Oxide Analyzer (Boulder, Colo.) by adding NO-releasing SNRs to deoxygenated PBS (pH=7.4 and 37° C.). Nitrogen was purged through the solution to carry liberated NO to the analyzer at a flow rate of 70 mL/min. Additional nitrogen flow was supplied to match the collection rate of the analyzer at 200 mL/min Real-time NO release profiles were recorded, allowing for the determination of NO release totals (t[NO]), half-lives ($t_{1/2}$), and maximum NO fluxes ($[NO]_{max}$).

f. Bactericidal Assays Under Static Conditions.

Cultures of *P. aeruginosa* and *S. aureus* were prepared as described previously.[6] (Privett, 2010) Briefly, bacterial cultures were grown from a frozen (−80° C.) stock overnight in TSB at 37° C. A 100 μL aliquot of the resulting suspension was added into 5 mL fresh TSB and incubated at 37° C. for ~2 h until the concentration reached $1\times10^8$ colony forming units (CFU)/mL, as confirmed by the OD600 and replicate plating and enumeration on nutrient agar. A working bacterial stock was generated by plating the bacterial suspension on TSA and incubating at 37° C. overnight. The TSA bacterial stocks were prepared weekly and stored at 4° C. For bactericidal assays, colonies of *P. aeruginosa* and *S. aureus* were taken from the TSA plate and dispersed in 3 mL TSB and then incubation at 37° C. overnight. A 100 μL aliquot of culture was added to 5 mL fresh TSB and incubated to a concentration of ~$1\times10^8$ CFU/mL. The bacteria was collected by centrifugation and resuspended in 3 mL PBS. The resulting suspension was diluted 100-fold in PBS to obtain a final concentration of $1\times10^6$ CFU/mL. The bactericidal efficacy of NO-releasing SNRs against the bacteria was evaluated after 4 h incubation over a range of concentrations. Bacteria suspensions in PBS were added to premeasured NO-releasing silica nanorods and incubated at 37° C. for 4 h. Following incubation, 100 μL aliquots of the bacteria suspensions were removed, diluted 10-fold in PBS, deposited on TSA plates, and incubated overnight at 37° C. The minimum concentration of NO-releasing SNRs that resulted in a 3-log reduction of bacterial viability after 4 h exposure was defined as the minimum bactericidal concentration (MBC).

g. In Vitro Toxicity

L929 mouse fibroblasts were grown in DMEM supplemented with 10% (v/v) fetal bovine serum (FBS) and 1 wt % penicillin/streptomycin, and incubated in 5% (v/v) $CO_2$ under humidified conditions at 37° C. After reaching 80% confluency, the cells were trypsinized, seeded onto tissue-culture treated polystyrene 96-well plates at a density of $3\times10^4$ cells/mL and incubated at 37° C. for 48 h. The supernatant was then aspirated prior to adding 200 μL fresh DMEM and 50 μL of a NO-releasing SNR suspension in PBS to each well. After incubation at 37° C. for 24 h, the supernatant was aspirated and 120 μL mixture of DMEM/MTS/PMS (105/20/1, v/v/v) was added to each well. The absorbance of the resulting colored solution after 1.5 h incubation at 37° C. was quantified at 490 nm using a Thermoscientific Multiskan EX plate reader. The mixture of DMEM/MTS/PMS and untreated cells were used as blank and control, respectively. The cell viability was calculated by equation 1.

$$\text{Cell Viability} = \frac{(Absorbance_{treated\ cell} - Absorbance_{blank})}{(Absorbance_{untreated\ cell} - Absorbance_{blank})} \quad \text{Eq. 1}$$

h. Confocal Microscopy for Detection of Intracellular NO.

Bacteria (*P. aeruginosa* and *S. aureus*) were cultured in TSB to a concentration of 1×10⁸ CFU/mL, collected via centrifugation (3645×g for 10 min), resuspended in sterile PBS, and adjusted to 1×10⁶ CFU/mL in PBS supplemented with 10 µM DAF-2 DA and 30 µM PI. The bacteria solution (2.5 mL) was incubated in a glass bottom confocal dish for 45 min at 37° C. A Zeiss 510 Meta inverted laser scanning confocal microscope with a 488 nm Ar excitation laser (2.0%) and a BP 505-530 nm filter was used to obtain DAF-2 (green) fluorescence images. Red fluorescence images for PI were obtained using a 543 nm HeNe excitation laser (25.3%) with a BP 560-615 nm filter. The bright field and fluorescence images were collected by a N.A. 1.2 C-apochromat water immersion lens with a 40× objective. Suspensions (1.5 mL) of AR1-c or AR8-c NO-releasing silica nanorods (44 µg/mL) in PBS (supplemented with 10 µM DAF-2 DA and 30 µM PI) were added to the bacteria solution (1.5 mL) in the glass confocal dish. Images were collected every 5 min to observe intracellular NO concentrations and cell death.

2. Synthesis of Diazeniumdiolate-Functionalized Silica Nanorods

Following SNR synthesis, the materials were functionalized with polyamine ligands to enable subsequent NO donor formation. The environment surrounding N-diazeniumdiolate NO donors can greatly influence NO-release kinetics particularly if manipulating water uptake and local pH. (Lu, 2011). Two distinct secondary amine functionalities were employed to determine SNR NO-release kinetics on bactericidal activity. Monoalkoxysilanes (i.e., N-(2-aminoethyl)-3-amino-isobutyl-imethylmethoxysilane (AEAI) and aminopropyldimethylethoxysilane (APDE)) were anchored onto the surface of SNR E, A, and B, denoted as AR1, AR4, and AR8, following a previously published modification procedure. (Li, C.; Han, J.; Ryu, C. Y.; Benicewicz, B. C., A versatile method to prepare RAFT agent anchored substrates and the preparation of PMMA grafted nanoparticles. *Macromolecules* 2006, 39, 3175-3183). Aminopropyldimethylethoxysilane (APDE)-functionalized rods containing only primary amines were further functionalized with acrylate-functionalized PEG, resulting in the formation of secondary amines (Scheme 1). (Lu, 2011). Varied NO-release kinetics were found from these two functionalities, as the degradation of N-diazeniumdiolate NO donors is related to the protonation of the polyamine that binds the NO. It is possible that more rapid water uptake/hydration by hydrophilic PEG chains on the surface of APDE-PEG functionalized SNRs would lead to faster N-diazeniumdiolate decomposition and NO release (i.e., higher [NO]max and shorter $t_{1/2}$). (Lu, 2011). Elemental analysis (Table 2) was used to determine the secondary amine content for AR1-a, AR4-a, AR8-a, AR4-b.

TABLE 2

Elemental analysis and zeta potential of the secondary amine-functionalized silica nanorods.

| | C (%) | H (%) | N (%) | 2°-amine content (µmol/mg) | Zeta Potential (mV) |
|---|---|---|---|---|---|
| AR1-a | 23.99 ± 1.41 | 5.38 ± 0.27 | 6.07 ± 0.18 | 2.19 ± 0.06 | 34.1 ± 1.6 |
| AR4-a | 23.16 ± 3.38 | 5.22 ± 1.20 | 5.77 ± 1.40 | 1.74 ± 0.42 | 35.2 ± 3.6 |
| AR8-a | 25.23 ± 5.50 | 5.47 ± 1.07 | 6.21 ± 1.22 | 2.43 ± 0.47 | 38.4 ± 1.2 |
| AR4-b | 18.80 ± 1.24 | 4.04 ± 0.45 | 2.14 ± 0.22 | 1.53 ± 0.16 | −8.1 ± 0.9 |

As shown in the scheme in FIG. 7, AR1-a, AR4-a, AR8-a, AR4-b were reacted or "charged" with NO at high pressures in methanol under basic conditions to form N-diazeniumdiolate functionalized nanorods (i.e., AR1-c, AR4-c, AR8-c, AR4-d). Next, chemiluminescence was used to characterize the NO storage and release properties of the N-diazeniumdiolate-modified SNRs (i.e., AR1-c, AR4-c, AR8-c, AR4-d) in PBS (pH 7.4, 37° C.). As shown in Table 3, the NO release totals and half-lives for AR1-c, AR4-c, and AR8-c were similar (~0.70 mmol/mg and ~0.70 h, respectively). In contrast, AR4-d had lower NO storage and a shorter half-life due to less secondary amine content (See Table 2). The secondary amine-to diazeniumdiolate conversion efficiency was similar (~20%) regardless of precursor concentration. Similar NO donor conversion values were previously reported for N-diazeniumdiolated-modified dendrimers. (Lu, 2011). The NO release profile of AR4-d showed the greatest initial flux (i.e., $[NO]_{max}$~14000 ppb/mg) and fastest decay (i.e., $t_{1/2}$=0.16 h), due to greater water uptake facilitated by the hydrophilic PEG groups. The distinct NO-release kinetics between AR4-c and AR4-d SNRs could thus affect NO flux-dependent bactericidal activity in addition to nanorod aspect ratio. Though AR1-c, AR4-c and AR8-c had similar $[NO]_{max}$, it has been found that nanorods with an aspect ratio of about 8 are surprisingly more bactericidal. Accordingly, certain geometries described fully herein have been found to be more effective. It is therefore contemplated that the functionalized nanorods having larger aspect ratios, for example, 9, 10, 11, 12, 13, 14, 15, 16, 17, 18, 19 or 20 will exhibit desirable bactericidal properties.

TABLE 3

Nitric oxide-release properties and surface charge (i.e., zeta potential) of N-diazeniumdiolate NO donor-functionalized SNRs.

| | t[NO]$^a$ (µmol/mg) | t[NO]$^b$ (µmol/mg) | $[NO]_{max}$ (ppb/mg) | $t_{1/2}$ (h) | Conversion (%) | Zeta Potential (mV) |
|---|---|---|---|---|---|---|
| AR1-c | 0.76 ± 0.12 | 0.63 ± 0.07 | 5400 ± 1100 | 0.77 ± 0.10 | 20 | −18.9 ± 0.7 |
| AR4-c | 0.69 ± 0.09 | 0.59 ± 0.07 | 5000 ± 800 | 0.70 ± 0.09 | 22 | −17.1 ± 0.9 |
| AR8-c | 0.77 ± 0.13 | 0.64 ± 0.09 | 5380 ± 700 | 0.76 ± 0.10 | 20 | −15.3 ± 0.4 |
| AR4-d | 0.36 ± 0.04 | 0.27 ± 0.03 | 14000 ± 1200 | 0.16 ± 0.01 | 24 | −20.8 ± 0.6 |

$^a$total NO storage per milligram particles.
$^b$total NO released after 4 h per milligram particles.

3. Bactericidal Activity as a Function of SNR Aspect Ratio

Figure 2:
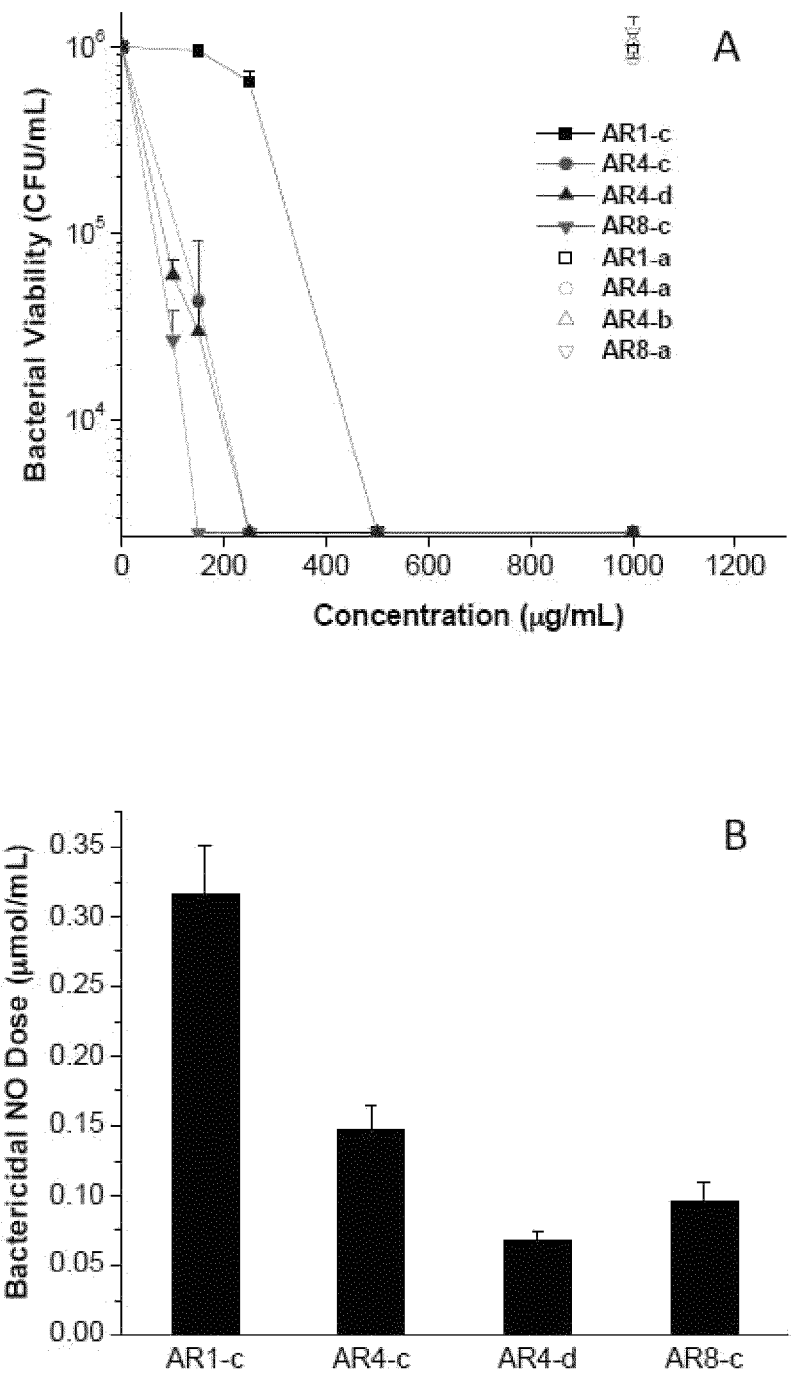
FIGS. 2A & B depict bacteria viability as a function of nanorod dose (A) and bacterial NO dose (B) of NO-releasing (solid symbols) SNRs against *P. aeruginosa* in PBS. Control nanorods (open symbols) resulted in no significant viability reduction at 1000 µg/mL.

Bacteria killing assays were evaluated in nutrient-free ("static") solutions with *P. aeruginosa*, a Gram-negative pathogen involved in burn and chronic wound infections. (Pruitt, B. A., McManus, A. T., Kim, S. H., Goodwin, C. W., Burn wound infections: Current status. *World J. Surg.* 1998, 22, 135-145; Lyczak, J. B.; Cannon, C. L.; Pier, G. B., Establishment of *Pseudomonas aeruginosa* infection: lessons from a versatile opportunist. *Microbes Infect.* 2000, 2, 1051-1060; Howell-Jones, R. S., Wilson, M. J., Hill, K. E., Howard, A. J., Price, P. E., Thomas, D. W., A review of the microbiology, antibiotic usage and resistance in chronic skin wounds. *J. Antimicrob. Chemother.* 2005, 55, 143-149) The minimum bactericidal concentration (MBC) reported represents the lowest dose of NO-releasing SNRs resulting in a 3 log reduction in bacteria viability after 4 h exposure. The corresponding dose of NO released from the SNRs over the 4 h is provided in FIG. 2B. As shown in FIG. 2, nanorods of higher aspect ratio killed bacteria at lower concentrations than lower-aspect ratio nanorods. For example, the MBCs for AR1-c, AR4-c, and AR8-c were 500, 250, and 150 µg/mL, respectively. The NO dose required to achieve a 3 log reduction in bacteria viability for AR8-c was ~0.10 mol/mL, lower than that of AR1-c (~0.32 µmol/mL) or AR4-c (~0.15 µmol/mL). The enhanced activity of AR8-c against *P. aeruginosa* may be attributed to greater contact area between the nanorod and the bacteria membrane, resulting in a greater NO dose delivered to the membrane. (Hetrick, 2008).

Figure 3:
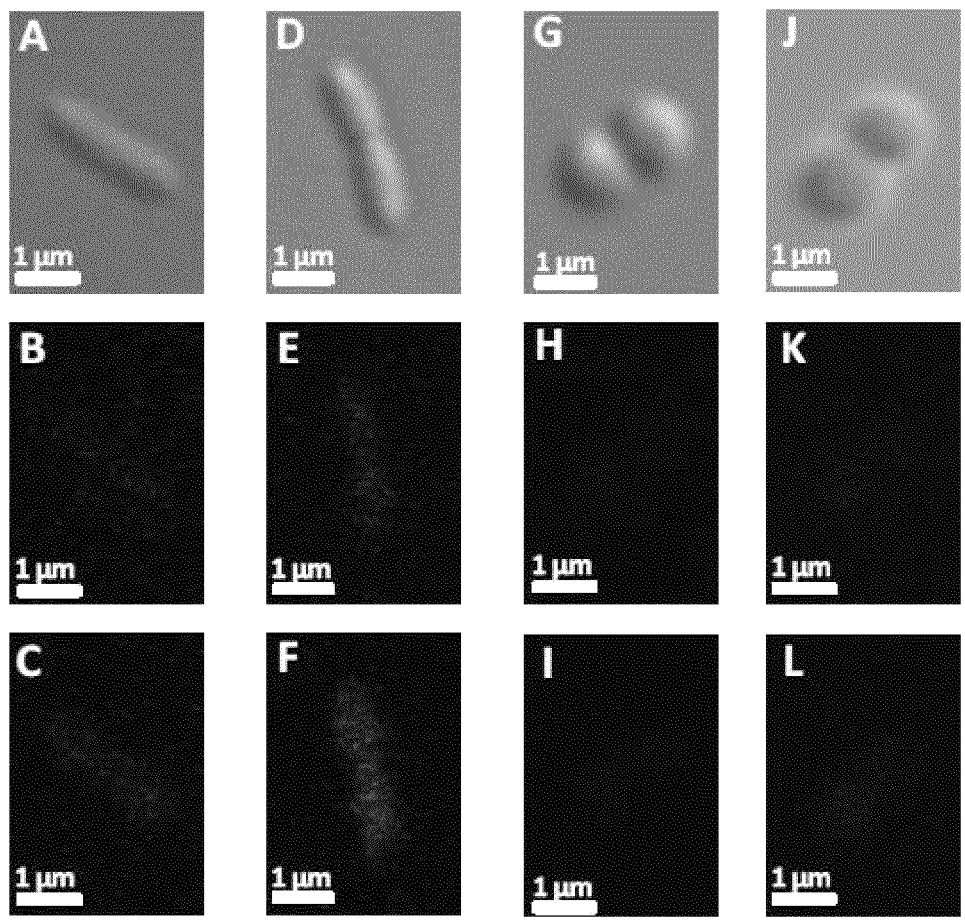
FIGS. 3A, B, C, D, E, F, G, H, I, J, K and L depict intracellular DAF-2 fluorescence from *P. aeruginosa* bacterial cells incubated with 22 µg/mL AR1-c (Bright filed (A), 120 min (B), 125 min (C)) and AR8-c (Bright field (D), 95 min (E), 100 min (F)) and from *S. aureus* bacterial cells incubated with AR1-c (Bright field (G), 135 min (H), 155 min (I)) AR8-c (Bright field (J), 100 min (K), 130 min (L)). Intensity of DAF-2 fluorescence indicates the intracellular concentration of NO and reactive nitrogen species.

Confocal microscopy was performed to confirm the greater NO delivery by AR8-c to the bacteria with the NO sensitive dye, 4,5-diaminofluorescein diacetate (DAF-2 DA). Briefly, the membrane-permeable DAF2-DA is hydrolyzed to the impermeable form, 4,5-diaminofluorescein (DAF-2), by intracellular esterases. In the presence of oxygen and NO, DAF-2 is converted to the green fluorescent derivative, triazolofluorescein. (Hetrick, 2008). As shown in FIG. 3, the intracellular NO delivered from AR8-c was observed at 95 min via DAF-2 fluorescence, ~25 min earlier than bacteria incubated with AR1-c. At 125 min, more than half of all the bacteria in view exhibited DAF-2 fluorescence compared to only one bacterium incubated with AR1-c (SI FIG. 1). The greater fluorescence intensity from bacteria incubated with AR8-c indicated larger intracellular NO concentrations (FIG. 3). As described previously by Fang (Fang, 1997), some of NO's antibacterial action is the result of NO reacting with superoxide, a product of bacteria respiration, to form peroxynitrite, a potent oxidative species that induces lipid peroxidation. The delivery of larger NO payloads to bacteria (e.g., by AR8-c) would accordingly lead to increased bactericidal activity. The corresponding secondary amine-functionalized control nanorods (AR1-a, AR4-a, AR8-a depleted of NO) exhibited no killing of *P. aeruginosa* at the MBCs of their NO-releasing counterparts (e.g., AR1-c, AR4-c, AR8-c).

4. Influence of NO-Release Kinetics

Figure 4:
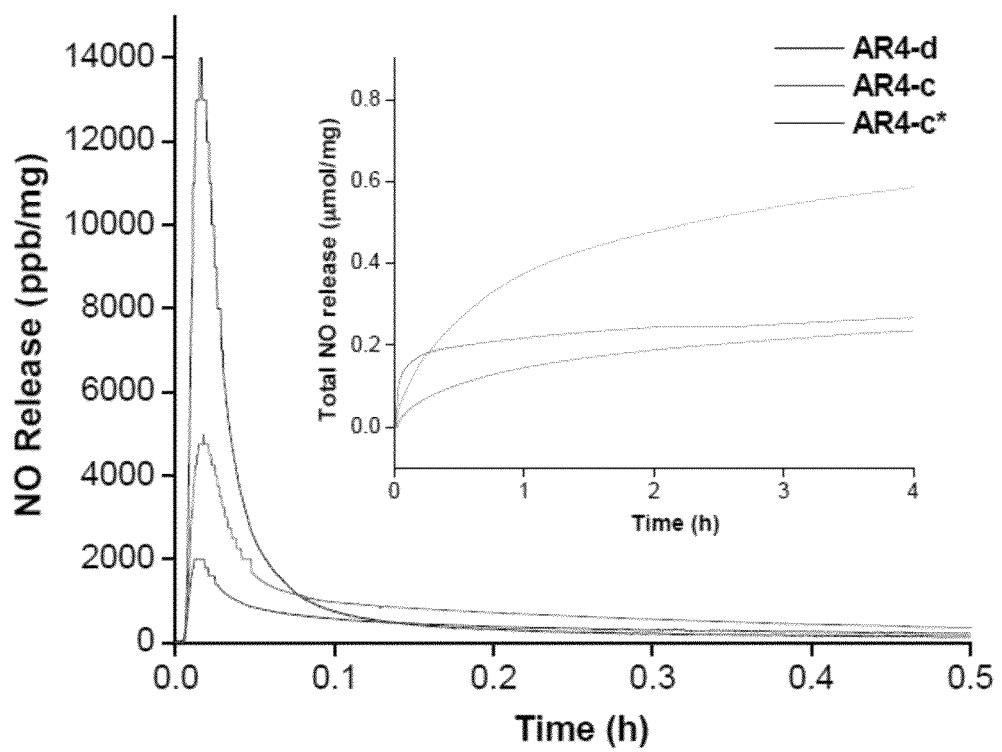
FIG. 4 depicts nitric oxide-releasing profiles of AEAI (c)- and APDE-PEG (d)-functionalized AR4 silica nanorods. Insert: total NO release of AR4-c, AR4-c* and AR4-d as a function of time.

In addition to studying shape-dependence, we sought to understand the influence of SNR NO-release kinetics on bactericidal activity. AR4-d and AR4-c SNRs with distinct NO-release profiles were thus exposed to *P. aeruginosa*. As shown in FIG. 4, AR4-d displayed greater initial NO flux ($[NO]_{max}$~14000 ppb/mg) and faster decay ($t_{1/2}$=0.16 h) due to the PEG modification and faster N-diazeniumdiolate breakdown. Bacteria killing assays against *P. aeruginosa* indicated that the bactericidal NO dose for AR4-d was approximately half that for AR4-c (~0.07 vs ~0.15 wand, respectively), suggesting that greater initial NO flux is favorable for killing *P. aeruginosa*. However, the total NO storage (e.g., t[NO]) for AR4-c was also greater than AR4-d. To rule out possible influence of NO release total, SNRs with similar t[NO] to AR4-d were prepared but with different $[NO]_{max}$, denoted as AR4-c*. As reported by Carpenter et al., (Carpenter, A. W.; Slomberg, D. L.; Rao, K. S.; Schoenfisch, M. H., Influence of Scaffold Size on Bactericidal Activity of Nitric Oxide-Releasing Silica Nanoparticles. *ACS Nano* 2011, 5 (9), 7235-7244) the total NO storage from a N-diazeniumdiolate macromolecule scaffold is tuned by altering the concentration of sodium methoxide. Reduced amounts of sodium methoxide (25 µL of 5.4 M sodium methoxide in methanol per 15 mg AR4-a nanorods) were used to prepare AR4-c*, thus matching the total NO storage of AR4-d (~0.27 mmol/mg). Since the resulting $[NO]_{max}$ for AR4-c* (2000 ppb/mg) was substantially lower than that of AR4-d (14000 ppb/mg), the comparison between AR4-d and AR4-c* shows the effect of NO flux on killing efficacy. The MBC for AR4-c* in a 4 h bacteria killing assay against *P. aeruginosa* was 4 mg/mL, substantially greater than that for AR4-d (0.25 mg/mL), illustrating the significance of a large initial NO flux (e.g., $[NO]_{max}$) for killing this bacterium.

In embodiments, nanorods AR4-c and AR4-d comprise the following pendant functionalized silanes and NO donor:

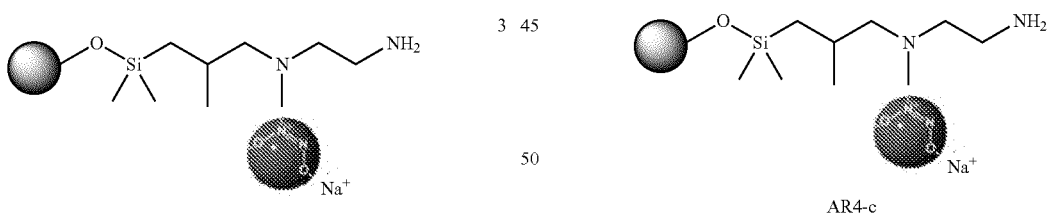

AR4-c

TABLE 4

| | | | P. aeruginosa | | S. aureus | |
|---|---|---|---|---|---|---|
| Particle 3 | $t[NO]^{4\ h}$ (µmol/mg) | $[NO]_{max}$ (ppb/mg) | MBC (µg/ml) | NO dosage (µmol/ml) | MBC (µg/ml) | NO dosage (µmol/ml) |
| AR1-c | 0.63 ± 0.07 | 5400 ± 1100 | 500 | 0.32 ± 0.04 | 2000 | 1.26 ± 0.14 |
| AR4-c | 0.59 ± 0.07 | 5000 ± 800 | 250 | 0.15 ± 0.02 | 1000 | 0.59 ± 0.07 |
| AR8-c | 0.64 ± 0.09 | 5380 ± 700 | 150 | 0.10 ± 0.01 | 300 | 0.19 ± 0.03 |

AR8 had the lowest MBC. Thus, it has the highest bactericidal efficacy. The MBC against *S. aureus* is higher than that against *P. aeruginosa*. MBC against *S. aurues* exhibited greater shape-dependence, though the preferred aspect ratio(s) exhibit more efficacy in general.

-continued

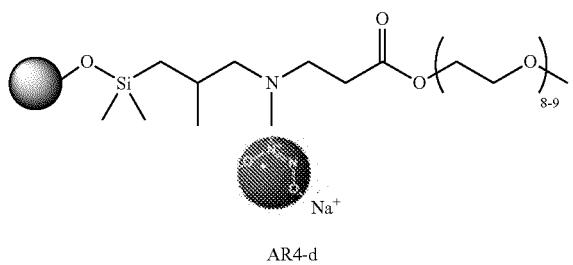

AR4-d

TABLE 5

| Particle | t[NO]$^{4h}$ (μmol/mg) | [NO]$_{max}$ (ppb/mg) | P. aeruginosa | | S. aureus | |
|---|---|---|---|---|---|---|
| | | | MBC (μg/ml) | NO dosage (μmol/ml) | MBC (μg/ml) | NO dosage (μmol/mg) |
| AR4-c | 0.59 ± 0.07 | 5000 ± 800 | 250 | 0.147 | 1000 | 0.586 |
| AR4-d | 0.27 ± 0.03 | 14000 ± 1200 | 250 | 0.067 | 500 | 0.134 |

Higher Initial flux provides higher bactericidal efficacy.
In embodiments, nanorods AR4-c* and AR4-d comprise the following pendant functionalized silanes and NO donor:

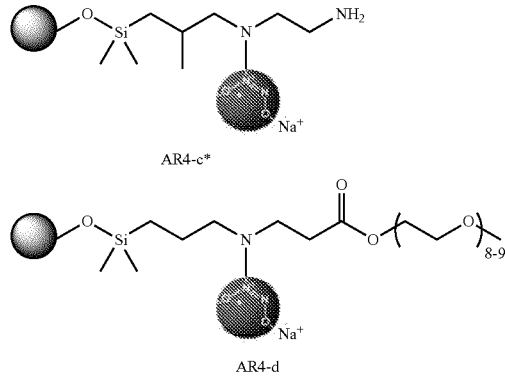

*Reduced NaOMe used in the synthesis of AR4-c* to match t[NO] of AR4-d.

TABLE 6

| Particle | t[NO]$^{4h}$ (μmol/mg) | [NO]$_{max}$ (ppb/mg) | P. aeruginosa | |
|---|---|---|---|---|
| | | | MBC (μg/ml) | NO dosage (μmol/ml) |
| AR4-c* | 0.27 ± 0.03 | 14000 ± 1200 | 250 | 0.067 |
| AR4-d | 0.24 ± 0.03 | 2000 ± 300 | 4000 | 0.92 |

5. Bacterial Assays Against S. Aureus

In contrast to P. aeruginosa, S. aureus is a Gram-positive bacteria with a thicker peptidoglycan layer and spherical morphology. (Bergey, D. H., Holt, J. G., Krieg, N. R., Sneath, P. H. A., Bergey's Manual of Determinative Bacteriology (9th ed.); Hensyl, W. R., Forlifer, L. E., Eds.; Lippincott Williams & Wilkins.: Baltimore, Md., 1994; pp 532-575). Privett et al. previously reported that NO produced from small molecule NO donors (e.g., 1-[2-(carboxylato)pyrrolidin-1-yl]diazen-1-ium-1,2-diolate (PROLI/NO)) was less effective at killing S. aureus compared to P. aeruginosa. (Privett, 2010). A high-aspect ratio SNRs may improve the bactericidal activity of the silica-based NO-releasing scaffolds against S. aureus by delivering NO more efficiently due to their shape.

As shown in FIG. 5, the MBCs for AR1-c, AR4-c, and AR8-c against S. aureus were 2000, 1000, and 300 μg/mL, respectively, greater than that against P. aeruginosa. We hypothesize that this behavior may be the result of decreased NO diffusion into the bacterium due to the more substantial (i.e., thicker) peptidoglycan layer for S. aureus. Confocal microscopy was used to characterize the NO diffusion to the inside of P. aeruginosa and S. aureus cells by monitoring the intracellular NO concentration as a function of time. As shown in FIG. 3, intracellular NO was observed more quickly for P. aeruginosa than S. aureus. Furthermore, the intracellular NO exhibited no significant increase from 110 to 130 min for S. aureus indicating slower NO diffusion.

Analogous to P. aeruginosa, AR8-c also delivered NO into the S. aureus cells more rapidly than AR1-c. As shown in FIG. 3, DAF-2 fluorescence appeared at 110 min compared to 135 min for AR1-c. As such, the AR8-c exhibited the greatest bactericidal activity. Overall, a more dramatic shape dependence of MBCs was observed against S. aureus, illustrating the influence of greater NO doses from high-aspect ratio nanorods (FIG. 3). The comparison between AR4-c and AR4-d shows the benefits of greater initial NO flux on bactericidal activity. Compared to PROLI/NO (Privett, 2010), each of the NO-releasing SNRs studied exhibited enhanced bactericidal activity against S. aureus. The bactericidal NO doses against S. aureus for AR1-c and AR4-c were 1.264 and 0.586 mmol/mL, respectively, roughly four times greater than that against P. aeruginosa. For AR8-c and AR4-d, the bactericidal NO doses against S. aureus were 0.191 and 0.134 mmol/mL, only twice that against P. aeruginosa. These results suggest that the more effective NO delivery (e.g., greater NO dose and flux) to the bacterium from NO-releasing SNRs may compensate for the lower bactericidal action of NO against Gram-positive S. aureus.

6. Mammalian Cell Cytotoxicity of NO

MTS assays were performed against L929 mouse fibroblasts over 24 h to evaluate the toxicity of the NO-releasing SNRs at the MBCs from the bactericidal assays. Nanorod concentrations were selected from 150 to 2000 μg/mL to encompass the bactericidal concentrations of the NO-releasing SNRs in PBS. The normalized cell viabilities after 24 h as a function of nanorod concentration are shown in FIG. 6. Nitric oxide-releasing SNRs (i.e., AR1-c, AR4-c, AR8-c, AR4-d) were not toxic at concentrations <500 μg/mL, while toxicity was observed at 1000 and 2000 μg/mL. Further inspection of the cytotoxicity and bactericidal assay results revealed that AR8-c and AR4-d were nontoxic at the MBCs against both P. aeruginosa and S. aureus. Although AR1-c and AR4-c were also nontoxic at the P. aeruginosa MBCs, reduced L929 cell viability was observed at the S. aureus MBCs. MTS assays were also used to assess the cytotoxicity of secondary-amine functionalized control nanorods. As shown in FIG. 6B, control nanorods also exhibited cytotoxicity at 1000 and 2000 μg/mL, explaining the toxicity of the NO-releasing SNRs. Collectively, the cytotoxicity results reinforce the advantage of AR4-d (e.g., high initial NO flux) and AR8-c (e.g., large aspect ratio) as antibacterial agents relative to AR4-c and AR1-c SNRs.

7. Size-Dependent Bactericidal Efficacy

Figure 10:
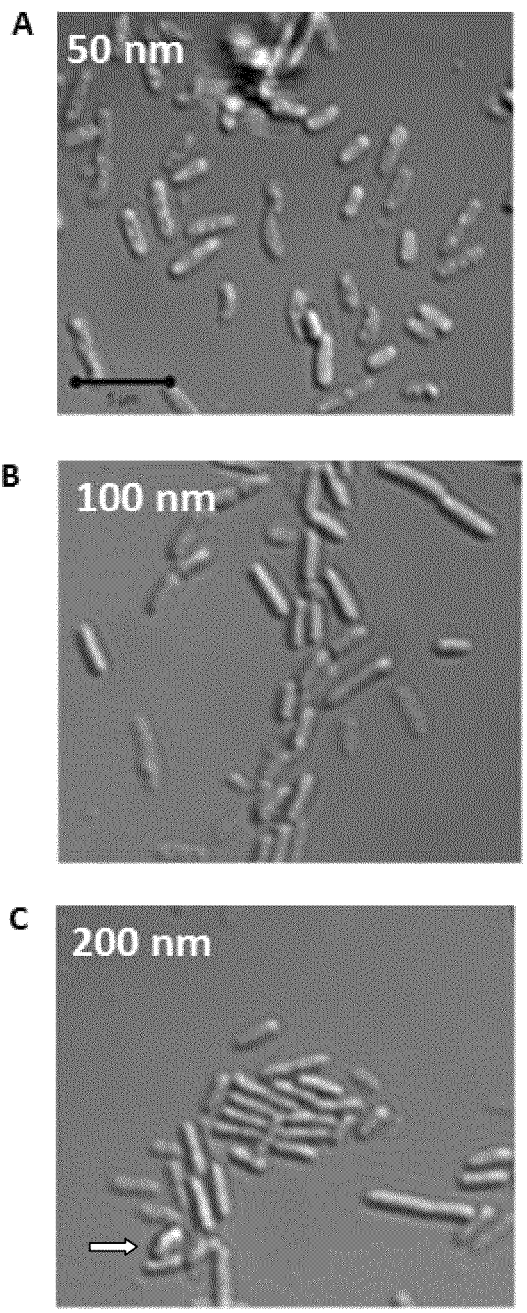
FIGS. 10A, B & C show the association of *P. aruginosa* with nanorods of different sizes.
Figure 11:
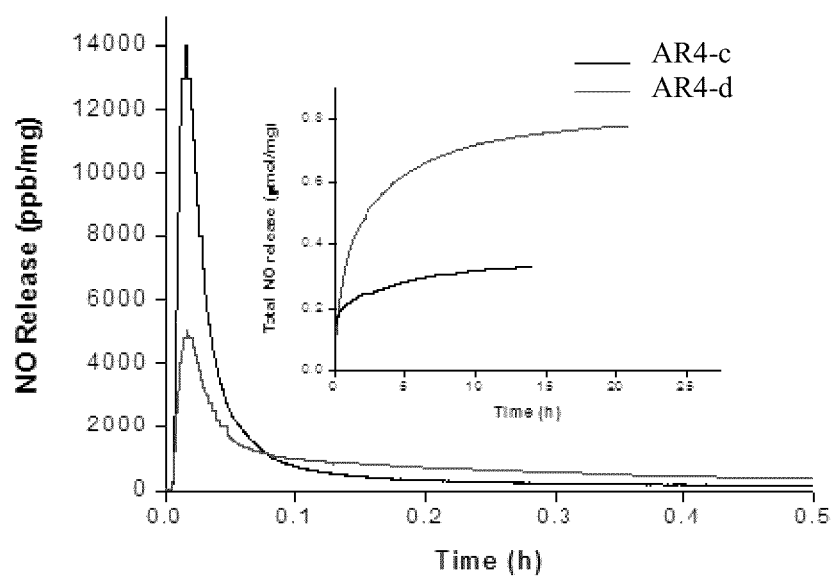
FIG. 11 depicts the effect of NO release over time.
Figure 12:
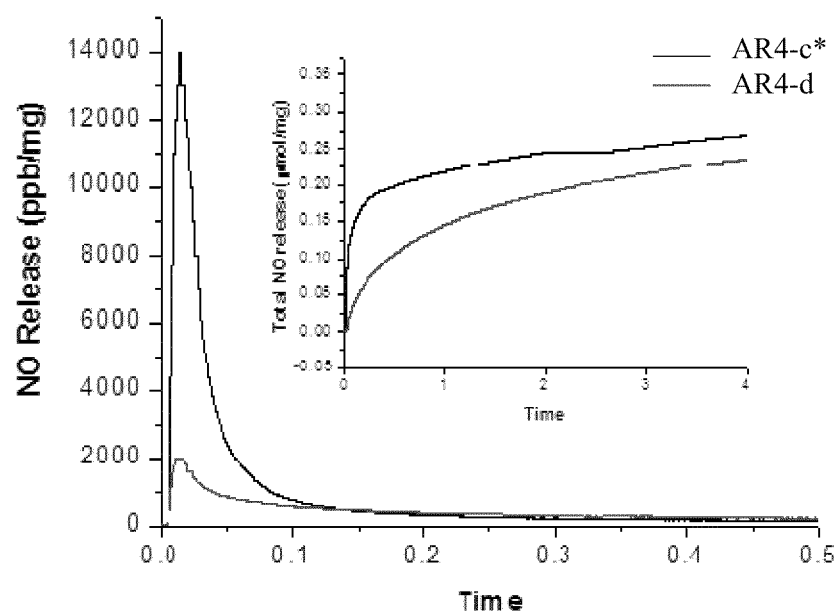
FIG. 12 depicts the effect of NO release over time.

Nanorods having different sizes were prepared (FIGS. 10A, B & C). Data for the bactericidal efficacy of these nanorods are provided in Table 7.

TABLE 7

| Particles (nm) | t[NO] (μmol/mg) | T[NO]$^{2\,h}$ (μmol/mg) | [NO]$_{max}$ (ppm/mg) | 2 h MBC (μmol/mg) | 24 h MBC (μg/ml) |
|---|---|---|---|---|---|
| 50 (FIG. 10A) | 1.49 ± 0.29 | 0.47 ± 16.8 | 49.7 ± 16.8 | 800 | 200 |
| 100 (FIG. 10B) | 1.26 ± 0.17 | 0.38 ± 0.01 | 43.5 ± 5.2 | 1500 | 400 |
| 200 (FIG. 10C) | 1.01 ± 0.08 | 0.42 ± 0.01 | 44.7 ± 8.0 | 1500 | 400 |

8. Anti-Biofilm Efficacy

As discussed above, the activity of the NO-releasing nanorods disclosed herein provides efficacy against biofilms though a higher amount of NO is required for eradication. The NO-releasing nanorods elicit about 70% viability reduction in mammalian cell viability at concentrations for biofilm eradication. Accordingly, the NO-releasing nanorods are safe for use.

| | P. aeruginosa | | S. aureus | |
|---|---|---|---|---|
| Scaffold | MBC$_{24\,h}$ (mg/mL) | Bactericidal NO Dose (μmol/mL) | MBC$_{24\,h}$ (mg/mL) | Bactericidal NO Dose (μmol/mL) |
| AR1 | 8 | 6.1 | 10 | 7.6 |
| AR4 | 2 | 1.6 | 4 | 2.5 |
| AR8 | 2 | 1.5 | 4 | 3.1 |

MBC: Minimum Bactericidal Concentration for 5-log (P. aeruginosa) or 4-log (S. aureus) reduction in biofilm bactericidal viability.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

That which is claimed:

1. A nitric oxide-releasing nanorod comprising,
   i. a silane, and
   ii. a functionalized mono, di or trialkoxysilane,
   wherein said functionalized mono, di or trialkoxysilane comprises a NO-donor molecule;
   wherein said nanorod has an aspect ratio of at least 1 and a [NO]$_{max}$ in a range of about 10 ppb/mg to about 16,000 ppb/mg.

2. The nanorod of claim 1, wherein said nanorod is mesoporous.

3. The nanorod of claim 2, wherein said mesoporous nanorod comprises pores having sizes from about 2 nm to about 50 nm in diameter.

4. The nanorod of claim 1, wherein said silane has the formula Si(OR)$_4$, wherein R is a C$_{1-5}$ alkyl.

5. The nanorod of claim 4, wherein said silane is TEOS or TMOS.

6. The nanorod of claim 1, wherein said silane is selected from the group consisting of methyltrimethoxysilane (MTMOS), ethyltrimethoxysilane (ETMOS), butyltrimethoxysilane (BTMOS), propyltrimethoxysilane (PTMOS), butyltriethoxysilane (BTEOS), and octadecyltrimethoxysilane (ODTMOS).

7. The nanorod of claim 4, wherein said functionalized mono, di or trialkoxysilane is a nitric oxide functionalized N-(2-aminoethyl)-3-amino-isobutyl-dimethylmethoxysilane (AEAI); aminopropyldimethylethoxysilane (APDE); N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl)phenethyltrimethoxysilane (AEMP3); [3-(methylamino)propyl]trimethoxysilane (MAP3); N-butylamino-propyltrimethoxysilane(n-BAP3); t-butylamino-propyltrimethoxysilane(t-BAP3); N-ethylaminoisobutyltrimethoxysilane(EAiB3); N-phenylaminopropyltrimethoxysilane (PAP3); and N-cyclohexylaminopropyltrimethoxysilane (cHAP3).

8. The nanorod of claim 1, wherein said aspect ratio is from about 4 to about 12.

9. The nanorod of claim 1, wherein said aspect ratio is about 8.

10. The nanorod of claim 1, wherein said nanorod has a [NO]$_{max}$ of from about 10 ppb/mg to about 14,000 ppb/mg.

11. The nanorod of claim 1, wherein said nanorod has a [NO]$_{max}$ of from about 3,000 ppb/mg to about 7,000 ppb/mg.

12. The nanorod of claim 1, wherein said nanorod has a length of less than about 1,700 nm.

13. The nanorod of claim 1, wherein said nanorod has a length of from 100 nm to about 1,300 nm.

14. The nanorod of claim 1, further comprising —(CH$_2$CH$_2$O)$_x$— that is covalently bound to said functionalized mono, di, or trialkoxysilane, wherein x is an integer from one to 10,000.

15. The nanorod of claim 14, wherein x is an integer from one to 50.

16. The nanorod of claim 1, wherein said NO donor is selected from the group consisting of a diazeniumdiolate, nitrosothiol, a nitrosamine, a hydroxyl nitrosamine, a hydroxyl amine, a hydroxyurea, and combination thereof.

17. The nanorod of claim 16, wherein said NO donor is selected from the group consisting of a diazeniumdiolate.

18. A method of preparing the nitric oxide-releasing nanorod of claim 1, comprising:
   a. contacting a silane with ammonia, sodium acetate, potassium acetate, sodium hydroxide or potassium hydroxide and mixtures thereof in the presence of a surfactant at a temperature $T_1$; to form a first composition;

b. allowing said first composition to age for a period of time, P, at a temperature $T_2$ to form a nanorod;

c. harvesting said nanorod;

d. contacting said harvested nanorod with a mono, di or trialkoxylsilane at a temperature, $T_3$, to form an amine-functionalized nanorod;

e. harvesting said amine-functionalized nanorod;

f. contacting said harvested amine-functionalized nanorod with NO gas to form a nitric-oxide releasing nanorod; and g. harvesting said nitric-oxide releasing nanorod.

19. A method of delivering nitric oxide to a subject, comprising:

administering an effective amount of said nitric oxide-releasing nanorod of claim 1 to said subject.

20. A method of treating a bacterial infection in a subject, comprising:

administering an effective amount of said nitric oxide-releasing nanorod of claim 1 to a subject in need thereof.

* * * * *